US012544233B2

(12) United States Patent
Corcoran et al.

(10) Patent No.: US 12,544,233 B2
(45) Date of Patent: Feb. 10, 2026

(54) SPINAL INTERBODY IMPLANTS

(71) Applicant: VB Spine US Opco LLC, Leesburg, VA (US)

(72) Inventors: Sean Corcoran, Ashburn, VA (US); Keith Fava, Purcellville, VA (US); Kenneth Dieselman, Reading, MA (US); Jennifer Anne Moore, Leesburg, VA (US); Amir Ali Sharifi-Mehr, Bloomingdale, NJ (US); Christopher P. Bell, New York, NY (US); Steven Willis, Jackson, NJ (US); Russell Simms, San Jose, CA (US); Justyna Zielinska, Bridgewater, NJ (US); Christian Karl Schultz, Denver, NJ (US); Clint Boyd, Leesburg, VA (US); Eleftherios Louvis, Carrigaline (IE); Leonid Pavlovsky, Parsippany, NJ (US); Joseph Henry Robinson, New City, NY (US)

(73) Assignee: VB Spine US Opco LLC, Leesburg, VA (US)

( * ) Notice: Subject to any disclaimer, the term of this patent is extended or adjusted under 35 U.S.C. 154(b) by 204 days.

(21) Appl. No.: 18/031,804

(22) PCT Filed: Oct. 13, 2021

(86) PCT No.: PCT/US2021/054765

§ 371 (c)(1),
(2) Date: Apr. 13, 2023

(87) PCT Pub. No.: WO2022/081695

PCT Pub. Date: Apr. 21, 2022

(65) Prior Publication Data

US 2023/0380983 A1 Nov. 30, 2023

Related U.S. Application Data

(60) Provisional application No. 63/091,551, filed on Oct. 14, 2020.

(51) Int. Cl.
*A61F 2/44* (2006.01)
*A61F 2/30* (2006.01)

(52) U.S. Cl.
CPC ....... *A61F 2/44* (2013.01); *A61F 2002/30011* (2013.01)

(58) Field of Classification Search
CPC ........ A61F 2/442; A61F 2/4455; A61F 2/446; A61F 2/4465; A61F 2/447; A61F 2/30771
See application file for complete search history.

(56) References Cited

U.S. PATENT DOCUMENTS 4,863,538 A 9/1989 Deckard
4,944,817 A 7/1990 Bourell et al.
(Continued)

FOREIGN PATENT DOCUMENTS

EP 1537839 A1 6/2005
WO 2017106780 A1 6/2017
(Continued)

OTHER PUBLICATIONS

International Search Report for Appln. No. PCT/US2021/054765 mailed Feb. 14, 2022 (4 pages).
(Continued)

*Primary Examiner* — Matthew J Lawson
(74) *Attorney, Agent, or Firm* — Lerner David LLP

(57) ABSTRACT

A spinal interbody implant includes an outer shell, a fill material disposed within the outer shell and a plurality of tubes extending from a first outer surface of the implant to
(Continued)

a second outer surface of the implant through the fill material. The fill material is more porous than the outer shell and the plurality of tubes.

19 Claims, 18 Drawing Sheets

(56) References Cited

U.S. PATENT DOCUMENTS 5,017,753 A 5/1991 Deckard
5,076,869 A 12/1991 Bourell et al.
5,607,424 A 3/1997 Tropiano
5,609,635 A 3/1997 Michelson
6,039,762 A 3/2000 McKay
6,136,031 A 10/2000 Middleton
6,494,883 B1 12/2002 Ferree
7,537,664 B2 5/2009 O'Neill et al.
9,987,051 B2 6/2018 Nunley et al.
D824,518 S 7/2018 Wilson et al.
10,028,841 B2 7/2018 Moore et al.
10,213,317 B2 2/2019 Bishop et al.
10,420,597 B2 9/2019 Papangelou et al.
10,512,545 B2 12/2019 Arnone
10,772,732 B1* 9/2020 Miller ................. A61F 2/30771
10,835,388 B2 11/2020 Milz et al.
11,826,265 B2* 11/2023 McLean .................. A61F 2/484
2002/0161443 A1 10/2002 Michelson
2003/0208274 A1* 11/2003 Davis ...................... A61F 2/442 623/17.16
2006/0052872 A1 3/2006 Studer et al.
2006/0129242 A1* 6/2006 Bergeron .............. A61F 2/0811 623/17.16
2007/0179610 A1* 8/2007 Biedermann ....... G02F 1/13458 623/16.11
2007/0260324 A1* 11/2007 Joshi ..................... A61F 2/4465 623/17.11
2008/0077244 A1 3/2008 Robinson
2008/0154379 A1 6/2008 Steiner et al.
2008/0161927 A1* 7/2008 Savage ................. A61F 2/4455 623/17.16
2010/0222750 A1 9/2010 Cheng
2012/0191188 A1* 7/2012 Huang .................... A61F 2/447 623/17.11
2012/0316650 A1 12/2012 Ullrich, Jr. et al.
2012/0330420 A1 12/2012 Brodke et al.
2013/0096685 A1 4/2013 Ciupik et al.
2013/0166793 A1* 6/2013 Shahar .................... G06F 13/28 710/26
2013/0304211 A1* 11/2013 Trautwein ............... A61L 27/04 623/17.15
2016/0038301 A1 2/2016 Wickham
2016/0128843 A1 5/2016 Tsau et al.
2016/0213405 A1 7/2016 Moore et al.
2016/0213487 A1* 7/2016 Wilson .................. A61F 2/4465
2016/0377113 A1 12/2016 Jimenez et al.
2017/0333205 A1* 11/2017 Joly .................... A61F 2/30771
2017/0354513 A1 12/2017 Maglaras et al.
2018/0110624 A1* 4/2018 Arnone ............... A61F 2/30771
2018/0256336 A1 9/2018 Mueller et al.
2018/0263785 A1 9/2018 Vishnubhotla et al.
2018/0296363 A1* 10/2018 Berry ........................ A61F 2/28
2018/0325692 A1 11/2018 Moore et al.
2019/0008562 A1 1/2019 Melton et al.
2019/0076258 A1* 3/2019 Black ...................... A61F 2/442
2019/0076266 A1* 3/2019 Trudeau .................... A61F 2/28
2019/0083282 A1 3/2019 Roeder et al.
2019/0183653 A1* 6/2019 Gregersen ............... A61F 2/447
2019/0343644 A1 11/2019 Ryan et al.
2019/0343645 A1 11/2019 Miccio et al.
2019/0343652 A1 11/2019 Petersheim et al.
2020/0038198 A1 2/2020 Miccio
2020/0046512 A1 2/2020 Newman et al.
2020/0289714 A1* 9/2020 Snell ................... A61F 2/30771
2021/0038403 A1* 2/2021 Neary ................... A61F 2/4455
2021/0077267 A1* 3/2021 Morrison .............. A61L 31/022
2021/0106433 A1* 4/2021 Motley ................... A61F 2/447
2021/0244548 A1* 8/2021 Ahn .................... A61F 2/30771
2022/0160519 A1* 5/2022 Northcutt ................ A61F 2/447
2022/0296386 A1* 9/2022 Fang ..................... A61F 2/4611
2023/0321324 A1* 10/2023 Reith ...................... A61L 27/18
2023/0404773 A1* 12/2023 Gantick .............. A61F 2/30771

FOREIGN PATENT DOCUMENTS

WO 2019165445 A1 8/2019
WO 2019191149 A1 10/2019

OTHER PUBLICATIONS

Partial International Search Report and Associated Communication issued in Appln. No. PCT/US2021/053153 dated Mar. 17, 2022 (13 pages).
International Search Report and Written Opinion issued in Appln. No. PCT/US2021/053153 mailed May 11, 2022 (20 pages).

* cited by examiner

SPINAL INTERBODY IMPLANTS

CROSS-REFERENCE TO RELATED APPLICATIONS

The present application is a national phase entry under 35 U.S.C. § 371 of International Application No. PCT/US2021/054765, filed Oct. 13, 2021, published in English, which claims priority to U.S. Application No. 63/091,551 filed Oct. 14, 2020, the disclosures of which are incorporated herein by reference.

BACKGROUND OF THE INVENTION

Back pain can be caused by many different maladies, some of which originate in the intervertebral discs of the spine. Typical problems with intervertebral discs include, among others, degeneration, bulging, herniation, thinning and abnormal movement. One widely used method of treatment for such disc problems is a spinal fusion procedure, whereby an affected disc is removed and the adjacent vertebral bodies are fused together through the use of interbody spacers, implants or the like.

The aforementioned implants often rely upon fixation elements to ensure engagement between the devices and the bone of the existing vertebral bodies. Because fixation elements are not a sufficient means for permanently securing the implant in place, fixation elements coupled with the normal compressive load of the spine act to keep the implant in place until bone can grow from the existing vertebral bodies into and through the implant. To encourage bone growth, the implants are often pre-loaded with bone growth promoting material and thereafter placed into the spine. Bone growth promoting material may include naturally occurring bone, artificial materials or the like.

To further ensure a strong implant-bone connection, some existing implants include porous material that promotes bone ingrowth. Although there is little doubt that bone ingrowth is beneficial in maintaining an implant in place, these implants are often very difficult and expensive to manufacture. Additionally, existing implants that include porous material often include such material in a limited manner. Often times, because of manufacturing or strength concerns or the like, the porous material is limited to a thin layer covering the upper and lower surfaces of the implant, which only allows for a small amount of bone to grow into the implant. Moreover, implants that utilize material that itself has a lower modulus of elasticity may suffer from reduced load bearing capacity.

Therefore, there exists a need for an improved spinal implant that provides improved bone ingrowth capacity while also having suitable load bearing capacity for use in spinal applications.

BRIEF SUMMARY OF THE INVENTION

The present disclosure relates to spinal implants and methods that involve use of same. In particular, the application relates to spinal implants made from a combination of porous and solid materials and the methods for fabricating such implants.

In one aspect, the present disclosure involves spinal interbody implants that include both solid and porous parts. Several embodiments are illustrated having various structures and configurations for optimizing the advantages of including both solid and porous regions in a body of an implant. Certain embodiments exploit the unique advantages of solid and porous materials having an outer structure made of a solid material with nominal porosity and an inner structure or inner region that has greater porosity and is disposed within the outer structure. Other embodiments of the spinal implants include alternating solid and porous regions. Such configurations include solid material for characteristics such as, e.g., improved load-bearing and porous material for, e.g., promoting bone in-growth, cell attachment and visibility in fluoroscopic imaging, among other purposes.

In a first example, an implant may have an outer shell. A fill material may be disposed within the outer shell. The implant may further include a plurality of tubes extending from a first outer surface of the implant to a second outer surface of the implant through the fill material. The fill material may be more porous than the outer shell and the plurality of tubes. In a second example, the plurality of tubes of the first example may include a first tube with a length entirely disposed within the fill material. In a third example, the plurality of tubes of the second example may include a second tube that extends through the outer shell and the fill material. In a fourth example, the second tube of the third example may be non-parallel to the first tube. In a fifth example, the first tube and the second tube of any of the third or fourth examples may intersect. In a sixth example, the plurality of tubes of any of the first through fifth examples may include a first tube that is filled with the fill material. In a seventh example, the plurality of tubes of any of the first through sixth examples may include a first tube with an outer surface and an inner surface, the outer surface having a shape different from the inner surface. In an eighth example, the outer surface of the seventh example may be cylindrical and the inner surface may be a triangular prism. In a ninth example, the implant of any of the seventh or eighth examples may also include a first channel that is non-parallel to the first tube. In a tenth example the first channel of the ninth example may extend through the outer shell and the fill material. In an eleventh example, the outer shell and the fill material of any of the first through tenth examples may be one of titanium or a titanium alloy. In a twelfth example, the outer shell of any of the first through eleventh examples may be formed of a first material and the fill material may be a second material, the first material being the same as the second material. In a thirteenth example, the first material of the twelfth example may be titanium. In a fourteenth example, the second material of any of the twelfth or thirteenth examples may be titanium.

In a first example of another embodiment, an implant may include an outer shell having a first endplate surface and a second endplate surface, the first endplate surface and the second endplate surface being separated by a lateral wall of the outer shell. A fill material may be disposed within the outer shell. A first plurality of channels may extend through the outer shell and the fill material with opposite ends at an outer surface of the lateral wall, the first plurality of channels being at a first distance from the first endplate surface. The implant may further include a second plurality of channels each having a length no greater than a thickness of the lateral wall, each of the second plurality of channels being at a second distance from the first endplate surface, the second distance being less than the first distance. The fill material may be more porous than the outer shell. In a second example, the fill material of the first example may include a first layer and a second layer enclosing the first layer, the first layer having a first porosity and the second layer having a second porosity less than the first porosity. In a third example, the first porosity of the second example may be between 55% and 65% and the second porosity may be between 20% and 50%.

In a first example of yet another embodiment, a spinal interbody implant may include an outer shell having a plurality of openings therein. The implant may have a fill material disposed in the outer shell, the fill material having a void therein. The outer shell may be deformable as a function of a force applied to an outer surface of the outer shell such that an increase in the force coincides with a decrease in a volume of the void. The fill material may be more porous than the outer shell. In a second example, the plurality of openings of the first example may have a depth equal to a thickness of the outer shell. In a third example, the fill material of any of the first or second examples may separate the void from a superior part of the outer shell and from an inferior part of the outer shell. In a fourth example, the void of any of the first through third examples may be fully enclosed by the outer shell. In a fifth example, the porous fill material of any of the first through fourth examples may form part of a superior surface of the implant and part of an inferior surface of the implant. In a sixth example, the outer shell and the fill material of any of the first through fifth examples may be one of titanium or a titanium alloy.

In a first example of yet another embodiment, a spinal interbody implant may include a core portion having a first porosity, the core portion having a plurality of channels extending from a first outer surface of the core portion to a second outer surface of the core portion. The implant may include a first material layer at least partially enclosing the core portion, the first material layer having a second porosity greater than the first porosity. The implant may include a second material layer at least partially enclosing the first material layer, the second layer having a third porosity different from the second porosity. In a second example, the first porosity of the first example may be the same as the third porosity. In a third example, the spinal interbody implant of any of the first or second examples may also include an inner core portion disposed within an opening through the core portion, the opening defined by an inner wall of the core portion, wherein the inner core portion has the second porosity. In a fourth example, the first outer surface and the second outer surface of any of the first through third examples may face the first material layer. In a fifth example, the plurality of channels of the fourth example may extend from a first outer surface of the second material layer to a second outer surface of the second material layer. In a sixth example, each of the first outer surface of the core portion and the second outer surface of the core portion of any of the first through fifth examples may be on an outer surface of the implant. In a seventh example, the core portion of any of the first through sixth examples may be an interior most layer of the implant. In an eighth example, the core portion and the first material layer of any of the first through seventh examples may be one of titanium or a titanium alloy.

In a first example of yet another embodiment, a spinal interbody implant may include an outer portion forming a first part of a top surface of the implant. The implant may further include an inner portion disposed within the outer portion, the inner portion forming a second part of the top surface of the implant. The implant may further include a first channel extending through the outer portion and the inner portion, a first end of the first channel being on a lateral surface of the implant and a second end of the first channel opposite the first end being on the top surface or a bottom surface of the implant. The inner portion may be more porous than the outer portion. In a second example, the first end of the first channel of the first example may be in the outer portion and the second end of the first channel is in the inner portion. In a third example, the inner portion of any of the first or second examples may include an inner surface defining a central opening. In a fourth example, the implant of the third example may further include a second channel that extends from a first end on the inner surface of the inner portion to a second end on the top surface or the bottom surface of the implant. In a fifth example, the first channel of any of the first through fourth examples may have a length that is less than half of a distance between the top surface of the implant and the bottom surface of the implant. In a sixth example, the outer portion and the inner portion of any of the first through fifth examples may be one of titanium or a titanium alloy.

In a first example of yet another embodiment, a spinal interbody implant may have a core portion including a first material matrix having a first porosity and a second material distributed throughout the first material matrix, the second material different from the first material, the first material having a first porosity. The implant may further have an inner peripheral portion enveloping the core portion, the inner peripheral portion including a third material and having a second porosity less than the first porosity. The implant may further have an outer peripheral portion enveloping the inner peripheral portion, the outer peripheral portion including a fourth material and a fifth material. In a second example, the first material and the third material of the first example may be polymers. In a third example, the first material of any of the first or second examples may be a polymer and the second material may be a metal or a metal alloy. In a fourth example, the fourth material of any of the first through third examples may be the same as the first material and the fifth material may be the same as the second material. In a fifth example, at least one of the first material and the second material of any of the first through fourth examples may be different from both of the fourth material and the fifth material. In a sixth example, the fourth material of any of the first through fifth examples may have a third porosity greater than the second porosity. In a seventh example, the fourth material of any of the first through sixth examples may be different from the fifth material. In an eighth example, the inner peripheral portion of any of the first through seventh examples may consist of the third material. In a ninth example, the first material of any of the first through eighth examples may be polyether ether ketone (PEEK), the second material may be titanium, and the core portion may further include a sixth material. In a tenth example, the sixth material of the ninth example may be Bioglass. In an eleventh example, the sixth material of the ninth example may be hydroxyapatite. In a twelfth example, the third material of any of the first through eleventh examples may be polyether ether ketone (PEEK). In a thirteenth example, the fourth material of the twelfth example may be the same as the first material, the fifth material may be the same as the second material, and the outer peripheral portion may further includes the sixth material.

In a first example of yet another embodiment, a spinal interbody implant may include a polymer matrix, a first material and a second material, the first material and the second material being distributed through the polymer matrix. The first material may be titanium. The second material may be bioglass or hydroxyapatite. In a second example, the body of the first example may be surrounded by a peripheral material layer, the peripheral material layer having material properties distinguishable from the body. In a third example, the body of any of the first or second examples may include a central void with a core material portion disposed therein, the core material portion having material properties distinguishable from the body.

In a first example of a method, a method of manufacturing a spinal interbody implant may include printing a first portion of the implant, the first portion being dissolvable; compression molding a second portion of the implant around the first portion such that the second portion entirely surrounds the first portion, the second portion including a matrix of a first material and a plurality of particles distributed throughout the matrix, the plurality of particles being a second material different from the first material; and dissolving the first portion subsequent to the compression molding step. In a second example, the first material of the first example may be a polymer and the second material may be a metal.

In a first example of another method, a method of manufacturing a spinal interbody implant may include conducting an additive manufacturing technique in a layer by layer fashion to form a complete intervertebral implant including formation of one or more layers having an outer perimeter ring, an inner fill material, and an inner ring within the inner fill material, the inner fill material having a porosity greater than that of the outer perimeter ring and the inner ring. In a second example, performance of the conducting step of the first example may occur through a single continuous process. In a third example, the forming of the one or more layers of any of the first or second examples may include forming the inner ring so that it is hollow. In a fourth example, the conducting step of the third example may include formation of additional layers until the inner ring becomes a tube, the tube being surrounded by the inner fill material. In a fifth example, the inner fill material of the fourth example may be disposed throughout a hollow passage through the inner tube.

DETAILED DESCRIPTION

Figure 1A:
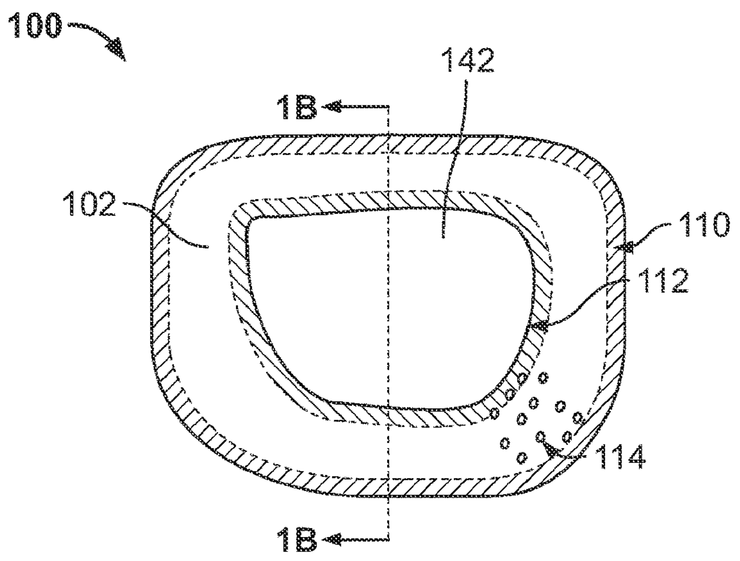
FIGS. 1A-B are top and cross-sectional views, respectively of a spinal implant according to one embodiment of the disclosure.

Reference will now be made to the embodiments of the present disclosure, including those illustrated in the accompanying drawings. Wherever possible, the same or like reference numbers will be used throughout the drawings to refer to the same or like features.

In describing embodiments of the disclosure, reference will be made to directional nomenclature used in describing the human body. It is noted that this nomenclature is used only for convenience and that it is not intended to be limiting with respect to the scope of the disclosure. For example, as used herein, when referring to the parts or ends of an implant, the term "anterior" means the end of an implant located toward the front of the body when implanted and the term "posterior" means toward the back of the body. The term "medial" means toward the midline of the body and the term "lateral" means toward the side or sides of the body. Additionally, in the drawings and in the description that follows, terms such as front, rear, upper, lower, top, bottom and similar directional terms are used simply for convenience of description and are not intended to limit the disclosure.

It should be appreciated that although specific examples provided throughout the disclosure reference spinal implants, methods of spinal access and related surgeries, the principles set forth herein are contemplated for application in other surgical approaches or in other areas of the body where similar access is required and/or where implants with a similar structure may be utilized.

In one aspect, the present disclosure relates to an intervertebral spinal implant. The implant may be manufactured having one or a combination of the structures discussed below in further detail. In some embodiments, the implant includes a solid part or portion and a porous part or portion. Use of the term "solid" to describe the solid part refers to its much lower porosity, by orders of magnitude, relative to the porous part. In some embodiments, the implants including both solid and porous portions are additively manufactured, as discussed further below. In this manner, an implant that includes both solid and porous portions may be manufactured through a single continuous process. In some variations of these embodiments, the solid portion may be constructed from titanium, a titanium alloy, a cobalt-chromium alloy, a ceramic, a polymer (e.g., polyetheretherketone) or any other suitable biocompatible material. The porous portion may be constructed from a titanium alloy, polymer, steel, cobalt chrome, an aluminum alloy and/or any other suitable biocompatible material. For example, the solid portion of an implant described in the embodiments herein may be a solid titanium, such as CASCADIA® by Stryker. And, the porous portion of an implant described in the embodiments herein may be a porous titanium alloy, such as TRITANIUM® by Stryker. The pores of the porous material may have an average pore diameter of 300-500 microns and an average porosity of up to 80%. In some examples, the pores of the porous material may have an average pore diameter of 400-500 microns and an average porosity of 55-65%. In some examples, the properties of a porous material matrix within the implant are consistent throughout the matrix with a fully interconnected porosity. Such a structure is advantageous in that it has an integrated surface roughness and allows for part-specific marking. In further specific examples, an implant may have titanium as a solid part and a titanium alloy as a porous part. However, in further examples, other suitable metals or non-metals may be used, such as those listed above.

Solid and porous portions of an intervertebral implant both have characteristics that can improve the performance of the implant. For example, the solid portion may mimic the physical characteristics of a cortical bone structure and provide a support structure that has load bearing capacity to withstand the weight borne by the spine when in use. The solid portion may form the outer shell of the implant, but may also include openings or through-holes to improve visibility of the implant in radiological imaging. The openings may be any suitable shape, such as diamond, circular, square, hexagonal, or the like. The porous portion provides improved visibility relative to the solid portion in radiological imaging. And, the porous portion further creates a favorable environment for promoting bone in-growth and proliferation to adhere and anchor the implant in a proper position between adjacent intervertebral bodies. Further, the porous portion has wicking properties so that biological fluids may be drawn into, absorbed and retained by the porous structure. During this process, the wicking properties may further cause the fluid to be distributed throughout the structure. When used in spinal interbody applications, the porous material may allow the structure to retain the biological fluids that result from endplate preparation. And, wicking characteristics of the spinal implant may allow for retention of this nutrient-rich fluid within the porous material matrix. Such characteristics may further accelerate recovery times and improve outcomes relative to implants lacking such properties through the distribution of nutrients against gravity and through the migration and attachment of cells to the implant. Accordingly, additional advantages may be realized when an implant includes solid and porous parts in a single implant.

Figure 1B:
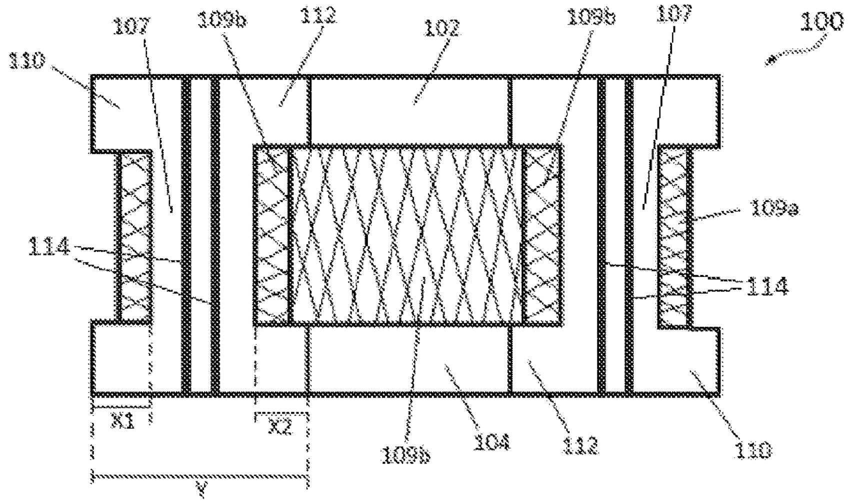

FIGS. 1A-B illustrate a spinal interbody implant 100 according to one embodiment of the disclosure. Implant 100 includes a superior contact plate 102 and an inferior contact plate 104, both of which are solid. As shown in FIG. 1A, superior contact plate 102 is annular with an outer circumference and an inner circumference. Superior contact plate 102 may further include an outer overhang 110 extending radially outward toward the outer circumference of superior contact plate 102 and an inner overhang 112 extending radially inward from the inner circumference of superior contact plate 102. Inferior contact plate 104, as best shown in FIG. 1B, a cross-sectional view of implant 100 along line 1B, may mirror the configuration of superior contact plate 102. In other examples, the implant may be different on each side of a bifurcation through line 1B. As shown in FIG. 1B, implant 100 further includes central solid portion 107 which extends around implant 100 between superior contact plate 102 and inferior contact plate 104 having a thickness defined by Y−(X1+X2). Central solid portion 107 optionally includes a series of channels 114 disposed through a depth of implant 100 between surfaces of the endplates, as described below in greater detail. Outer overhangs 110 have a width X1 and inner overhangs 112 have a width X2. Porous parts 109*a*, 109*b*, described in greater detail below, may be optionally disposed within the overhangs, as shown in FIG. 1B, typically so that the outer surface of porous parts 109*a*, 109*b* are recessed relative to a free end of the respective overhangs. In the illustrated embodiment, X1 is equal to X2. However, it is contemplated that X1 and X2 may not be equal. X1 and X2 may have any values such that the sum of X1 and X2 is still less than Y so that at least a portion of central solid portion 107 remains to provide stability for implant 100.

Porous portions 109*a*, 109*b* are porous relative to central solid portion 107 and are disposed between superior contact plate 102 and inferior contact plate 104 to promote circumferential fusion of implant 100 to bone material. Inner porous portion 109*b* extends around the inner circumference of central solid portion 107 and outer porous portion 109*a* extends around the outer circumference of central solid portion 107. As illustrated in FIG. 1B, outer overhang 110 is disposed superior and inferior to outer porous portion 109*a*, and inner overhang 112 is disposed superior and inferior to inner porous portion 109*b*. Thus, outer and inner porous portions 109*a*, 109*b* extend a height between outer overhang 110 and inner overhang 112, respectively. It is contemplated that porous portions 109*a*, 109*b* may extend any height between superior contact plate 102 and inferior contact plate 104.

Implant 100 may optionally include channels 114 extending from superior contact plate 102 to inferior contact plate 104. These channels may be understood to have a lamellar characteristic and may be patterned and sized to achieve desired performance in that respect. In one example, a series of channel pairs extend through a depth of the implant at regular intervals around a perimeter of central solid portion 107, as shown at one location in FIG. 1B. Channels 114 may be disposed in pairs around the circumference of implant

100, each pair spaced equal distances apart from adjacent pairs. Alternatively, channels 114 may be disposed in groups, e.g., two adjacent pairs, wherein each group of channels is spaced together but a larger distance away from adjacent groups. Other spacing arrangements between channel pairs are also contemplated. In other examples, channels 114 may not be in pairs, but may be a series of individual channels positioned at various locations throughout implant 100. In still further examples, channels 114 may be disposed in a grid formation spaced equal distances apart while oriented in a superior-inferior direction through the implant. Although channels 114 are illustrated in one region of implant 100 in FIG. 1A, vertical channels 114 may be included around the entire implant 100 through central solid portion 107. The solid part of implant 100, inclusive of contact plates 102, 104 and central solid portion 107, defines an I-shaped cross-section extending around the implant perimeter, shown at one section in FIG. 1B. Channels 114 are positioned through central solid portion 107 and extend between superior contact plate 102 and inferior contact plate 104. The I-shape formed by central solid portion 107 and contact plates 102, 104 provides improved bending capacity of implant 100 relative to implant shapes without flanges away from the center, such as rectangular shaped sections. Thus, the expected longevity of the implant when implanted in a spine of a patient is increased accordingly. The implant may include a void interior to inner porous portion 109*b* to create a graft window 142 through the implant. Alternatively, in some examples, material used for the inner and outer porous portions may be disposed throughout the volume of the graft window so that there is no window through a central region of the implant.

Figure 1C:
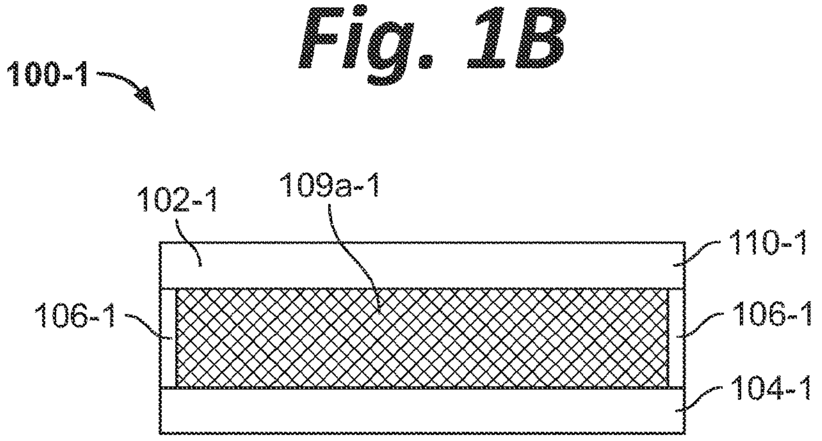
FIG. 1C is a side view of a spinal implant according to a variation of the implant of FIG. 1A.

In a variation of implant 100, FIG. 1C illustrates implant 100-1 with side struts 106-1. Struts 106-1 extend between overhangs 110-1 of the superior contact plate 102-1 and of the inferior contact plate 104-1. The struts 106-1 may be included to provide extra structural support for the implant, particularly when the included overhangs represent a significant dimension relative to that of the overall implant. The struts may be a series of post-type structures spaced at regular intervals around the implant perimeter and may have a width commensurate with the materials chosen and based on a radial dimension of the strut, all with a view to satisfaction of the desired load bearing capacity. In some examples, the struts are only on the outer perimeter of the implant adjacent to the outer porous portion. In other examples, the struts are only on the inner perimeter of the implant adjacent to the inner porous portion. In still further examples, the struts are along both the outer and inner perimeters of the implant.

Figure 22A:
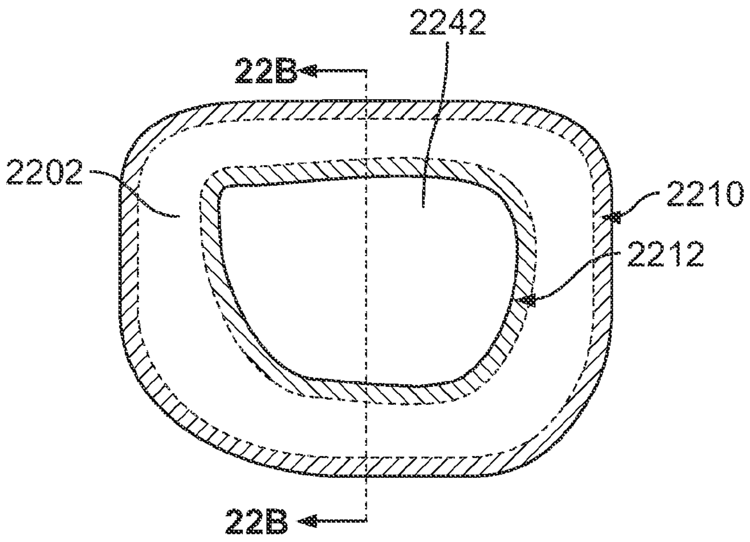
FIGS. 22A-B are top and cross-sectional views, respectively, of a spinal implant according to an embodiment of the disclosure.
Figure 22B:
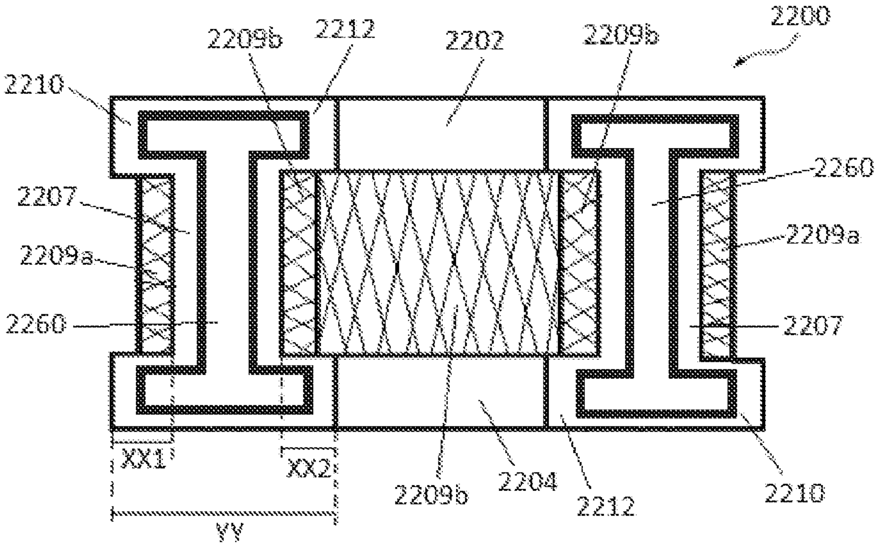

FIGS. 22A-B illustrate a spinal interbody implant 2200 according yet another embodiment of the disclosure. Unless otherwise stated, like reference numerals refer to like elements of above-described intervertebral implant 100, but within the 2200-series of numbers. Implant 2200 includes a superior contact plate 2202 and an inferior contact plate 2204, both of which are solid. As shown in FIG. 22A, superior contact plate 2202 is annular with an outer circumference and an inner circumference. Superior contact plate 2202 further includes an outer overhang 2210 extending radially outward toward the outer circumference of superior contact plate 2202 and an inner overhang 2212 extending radially inward from the inner circumference of superior contact plate 2202. Inferior contact plate 2204, as best shown in FIG. 22B, a cross-sectional view of implant 2200 along line 22B, mirrors the configuration of superior contact plate 2202, although in some examples it may vary. As shown in FIG. 22B, implant 2200 further includes central solid portion 2207 which extends around implant 2200 between superior contact plate 2202 and inferior contact plate 2204 having a thickness defined by YY−(XX1+XX2). The solid part of implant 2200, inclusive of contact plates 2202, 2204 and central solid portion 2207, defines an I-shaped cross-section extending around the implant perimeter, shown at one section in FIG. 22B. The I-shaped structure includes a hollow I-shaped region 2260 therein which is coextensive with the I-shaped structure around the implant 2200 perimeter. The I-shape formed by central solid portion 2207 and contact plates 2202, 2204 provides improved bending capacity of implant 2200 as described above for implant 100. Further, the hollow characteristic of the I-shaped section provides the benefit of increased bending capacity while also reducing the overall weight of the implant.

Outer overhangs 2210 have a width XX1 and inner overhangs 2212 have a width XX2. Porous portions 2209*a*, 2209*b*, described in greater detail below, are disposed within the overhangs, as shown in FIG. 22B, typically so that the outer surface of porous parts 2209*a*, 2209*b* are recessed relative to a free end of the respective overhangs. In the illustrated embodiment, XX1 is equal to XX2. However, it is contemplated that XX1 and XX2 may not be equal. XX1 and XX2 may have any values such that the sum of XX1 and XX2 is still less than YY so that at least a portion of central solid portion 2207 remains to provide stability for implant 2200.

Implant 2200 further includes outer porous portion 2209*a* and inner porous portion 2209*b*. Porous portions 2209*a*, 2209*b* are porous relative to central solid portion 2207 and are disposed between superior contact plate 2202 and inferior contact plate 2204 to promote circumferential fusion of implant 2200 to bone material. Inner porous portion 2209*b* extends around the inner circumference of central solid portion 2207 and outer porous portion 2209*a* extends around the outer circumference of central solid portion 2207. As illustrated in FIG. 22B, outer overhang 2210 is disposed superior and inferior to outer porous portion 2209*a*, and inner overhang 2212 is disposed superior and inferior to inner porous portion 2209*b*. Thus, outer and inner porous portions 2209*a*, 2209*b* extend a height between outer overhang 2210 and inner overhang 2212, respectively. It is contemplated that porous portions 2209*a*, 2209*b* may extend any height between superior contact plate 2202 and inferior contact plate 2204. Implant 2200 may include a void interior to inner porous portion 2209*b* to create a graft window 2242 through the implant. Alternatively, in some examples, material used for the inner and outer porous portions may be disposed throughout the volume of the graft window so that there is no window through a central region of the implant.

In some examples, it is contemplated that the channels of implants 100, 100-1, 2200 may be oriented in a lateral direction and incorporated through the lateral walls, e.g. from one lateral side to another or from the anterior wall to the posterior wall of the implant. The channels may also extend from the superior contact plate to the inferior contact plate in a transverse orientation, i.e., non-parallel with an axis through a length of the spine. The channels may also be oriented transverse to each other, such that the channels intersect. The channels may vary in size and location, such that the channels are more concentrated on some portions of the implant surfaces than others. The channels may be hollow, filled with the material used for the porous portion or filled with another porous material. In some examples, the implant does not include lateral walls and is supported entirely by the structure of the porous portion extending through the region between the superior and inferior contact plates. The number, shape and patterns of the channels on the implant may be varied in many ways. Non-limiting examples of such arrangements may be found in U.S. Pat. Nos. 10,028,841 and 9,987,051, Design Pat. No. D824,518 and U.S. Pat. Appl. Publ. Nos. 2020/0046512, 2018/0325692, 2016/0213487 and 2016/0213405, the entire disclosures of which are hereby incorporated by reference herein.

Figure 2A:
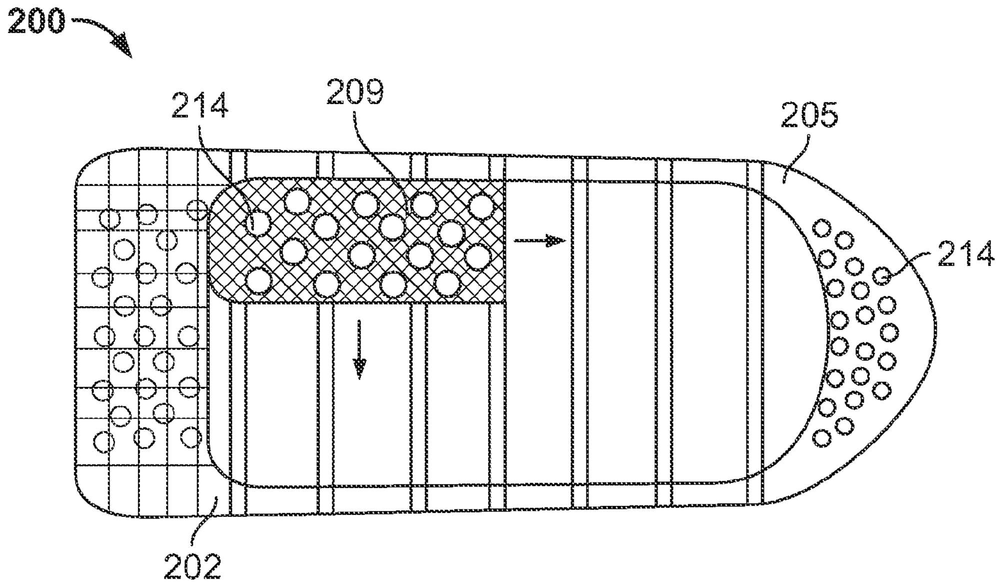
FIGS. 2A-B are top and side cross-sectional views, respectively, of a spinal implant according to an embodiment of the disclosure.
Figure 2B:
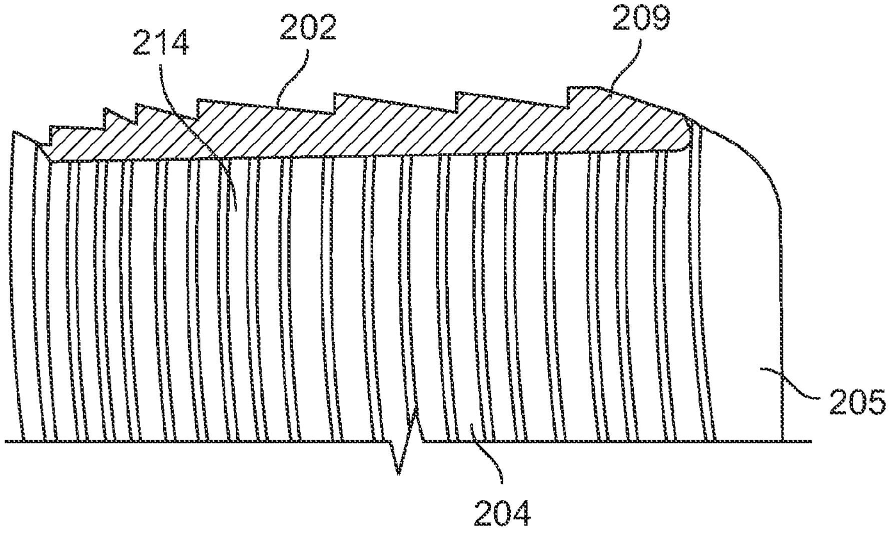

FIGS. 2A-B illustrate an implant 200 according to another embodiment of the disclosure. Unless otherwise stated, like reference numerals refer to like elements of above-described intervertebral implant 100, but within the 200-series of numbers. Implant 200 may be bullet-shaped, comprising a porous portion 209 and a solid portion 205. In some examples, a particular outer shape of implant 200 may vary from that shown. Solid portion 205 may include a recessed part on superior surface 202 and porous portion 209 is formed therein. Porous portion 209 is porous and is sized to maximize its surface contact with an adjacent vertebral body when implanted in a patient. The porous portion further provides for wicking and enhanced cellular attachment as described above. The implant may optionally include channels 214 extending through implant 200 in a superior-inferior direction between superior surface 202 and inferior surface 204 which improves radiolucency as described above. In the depicted embodiment, channels 214, are hollow, but in some examples, the channels may be filled with porous material. In some examples, the implant may further include at least one laterally oriented channel which extends from one lateral surface to another. The lateral channel may intersect with a vertical channel. The channels may be arranged in a grid formation spaced equal distances apart from each other along the solid portion and/or the porous portion. It is also contemplated that, in some examples, the implant may include one or more channels through the solid portion but not the porous portion. The channels may also be oriented at angles transverse to the surfaces of the implant or transverse to each other. The channels may also be nonlinear.

Figure 3A:
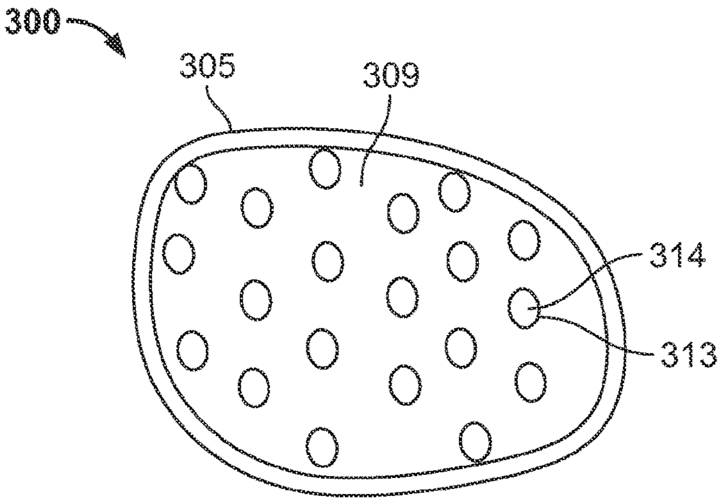
FIGS. 3A-B are top and side views, respectively, of a spinal implant according to an embodiment of the disclosure.
Figure 3B:
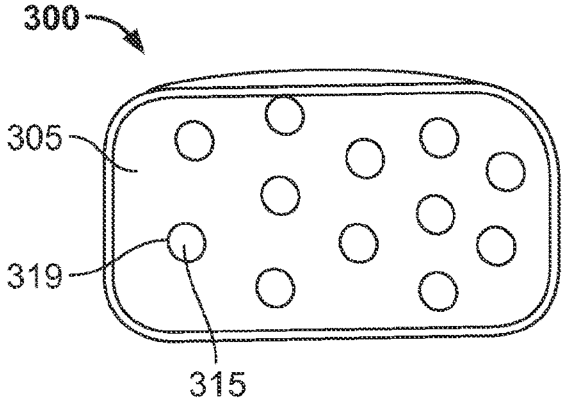

FIGS. 3A-B illustrate an implant 300 according to yet another embodiment of the disclosure. Unless otherwise stated, like reference numerals refer to like elements of above-described intervertebral implants 100 and 200, but within the 300-series of numbers. Implant 300 includes a porous portion 309 and a peripheral portion 305 enveloping porous portion 309. Porous portion 309 is porous, whereas peripheral portion 305 is solid. Implant 300 further includes solid tubular structures 313 with vertical channels 314 therethrough, tubular structures 313 extending through a depth of the implant. Each tubular structure 313 is disposed within porous portion 309, as shown in FIG. 3A. Similar solid tubular structures 319, with lateral channels 315 therein, pass laterally through sides of implant 300. Tubular structures 319 may pass through both peripheral portion 305 and porous portion 309, though in some examples, peripheral portion 305 may include separate holes to connect tubular structures 319 with the external surface of the implant. Implant 300 also includes tubular structures 319 oriented laterally and extending through the body of implant 300. As with tubular structures 313, tubular structures 319 are solid. Tubular structures 319 define lateral channels 315. In some examples, some or all of channels 315 intersect with channels 314. In other examples, channels 315 do not intersect with channels 314. In some examples, channels 314, 315 are 1 millimeter in diameter, but any size and/or shape is contemplated. Both vertical and lateral channels 314, 315 may be hollow and thereby improve radiolucency of implant 300. The channels may be arranged in a grid formation spaced equal distances apart from each other or patterned in any suitable arrangement throughout the porous portion and the peripheral portion. The channels may extend in directions transverse to the surfaces of the implant and/or transverse to each other. The channels may also be nonlinear In one example, an Implant 300 may comprise an outer shell or peripheral portion 305, a fill material or porous portion 309 disposed within the outer shell 305, and a plurality of tubes 313, 319 extending from a first outer surface of the implant to a second outer surface of the implant through the fill material 309, wherein the fill material 309 is more porous than the outer shell 305 and the plurality of tubes 313, 319.

Figure 4:
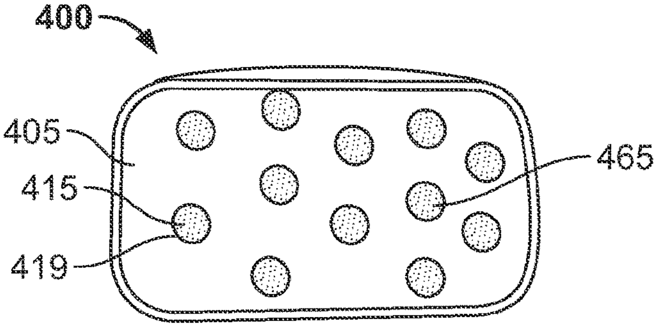
FIG. 4 is a side view of a spinal implant according to an embodiment of the disclosure.

FIG. 4 illustrates an implant 400 according to yet another embodiment of the disclosure. Unless otherwise stated, like reference numerals refer to like elements of above-described intervertebral implants 100, 200 and 300, but within the 400-series of numbers. Implant 400 is substantially similar to implant 300 depicted in FIGS. 3A-B. Implant 400 includes laterally extending tubular structures 419, with channels 415 therein, wherein the channels are filled with a porous fill 465. In some examples, it is contemplated that vertical tubular structures (not shown) of the implant, when included, may also be filled with the porous fill material. In one example, an Implant 400 may comprise an outer shell or peripheral portion 405, a fill material or porous portion disposed within the outer shell 405, and a plurality of tubes 419 extending from a first outer surface of the implant to a second outer surface of the implant through the fill material, wherein the fill material is more porous than the outer shell 405 and the plurality of tubes 419.

Figure 5A:
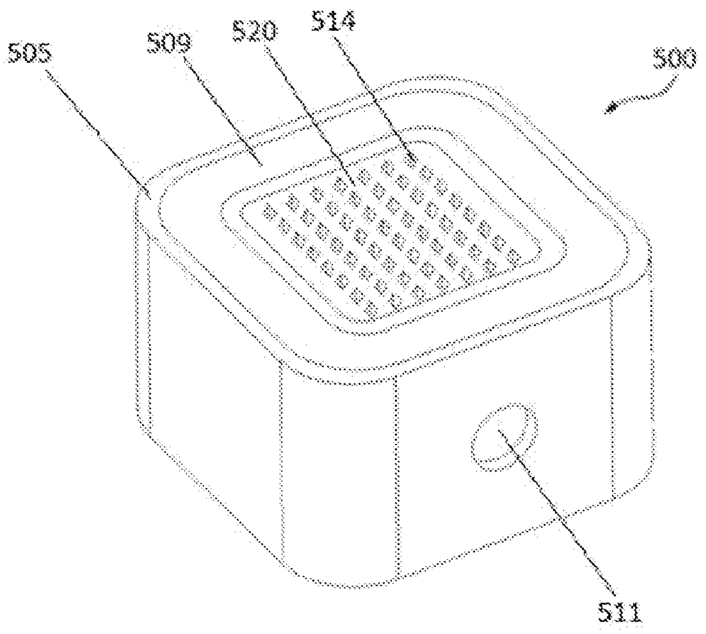
FIG. 5A is a perspective view of a spinal implant according to an embodiment of the disclosure.
Figure 5B:
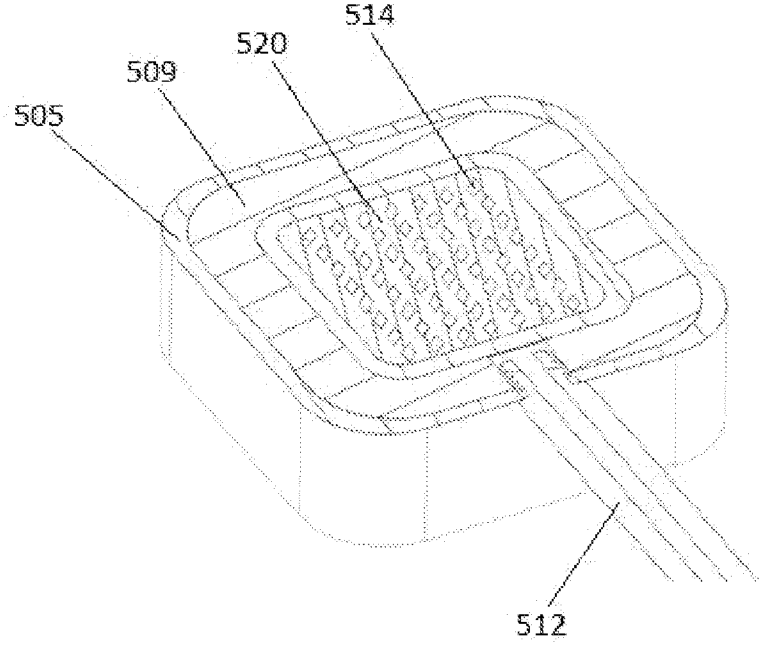
FIG. 5B is a perspective sectional view of the implant of FIG. 5A.

FIGS. 5A-B illustrate an implant 500 according to yet another embodiment of the disclosure. Unless otherwise stated, like reference numerals refer to like elements of above-described intervertebral implants 100, 200 and 300, but within the 500-series of numbers. Implant 500 may be generally rectangular in shape with beveled corners or may have another shape to suit a patient anatomy, such as an elliptical or oblong shape. The implant includes an interior body 520, a porous layer portion 509 peripherally wrapped around interior body 520 and a peripheral portion 505 peripherally wrapped around porous layer portion 509. Interior body 520 and peripheral portion 505 are solid, and porous layer portion 509 is porous. Interior body 520 may optionally include channels 514 that extend in a superior-inferior direction through implant 500. Channels 514 are diamond-shaped and arranged in a grid formation spaced equal distances apart from each other across interior body 520. In some examples, the channels may have other shapes. Implant 500 defines a passage 511 as shown in FIG. 5A. Passage 511 is configured to receive an injection instrument 512, as shown in FIG. 5B to deliver a liquid such as bone marrow aspirate into interior body 520 or porous layer portion 509. It is also contemplated that the channels may be any shape, such as cylindrical, triangular, rectangular, etc. The channels may be more highly concentrated in some sections of the interior body than others. The channels may be included in the porous layer portion and/or the peripheral portion. The channels may extend at angles transverse to the surfaces of the implant or each other, and the channels may be nonlinear. Porous layer portion 509 has a thickness defined as the distance porous layer portion 509 extends between interior body 520 and peripheral portion 505. In some examples, a ratio of a thickness of the porous layer portion to the interior body may vary from that shown in FIGS. 5A-5B. In one example, a spinal interbody implant

500 may comprise a core portion or interior body 520 having a first porosity, the core portion 520 including a plurality of channels 514 extending from a first outer surface of the core portion 520 to a second outer surface of the core portion 520, a first material layer 509 at least partially enclosing the core portion 520, the first material layer 509 having a second porosity greater than the first porosity, and a second material layer 505 at least partially enclosing the first material layer 509, the second layer 505 having a third porosity different from the second porosity.

Figure 6A:
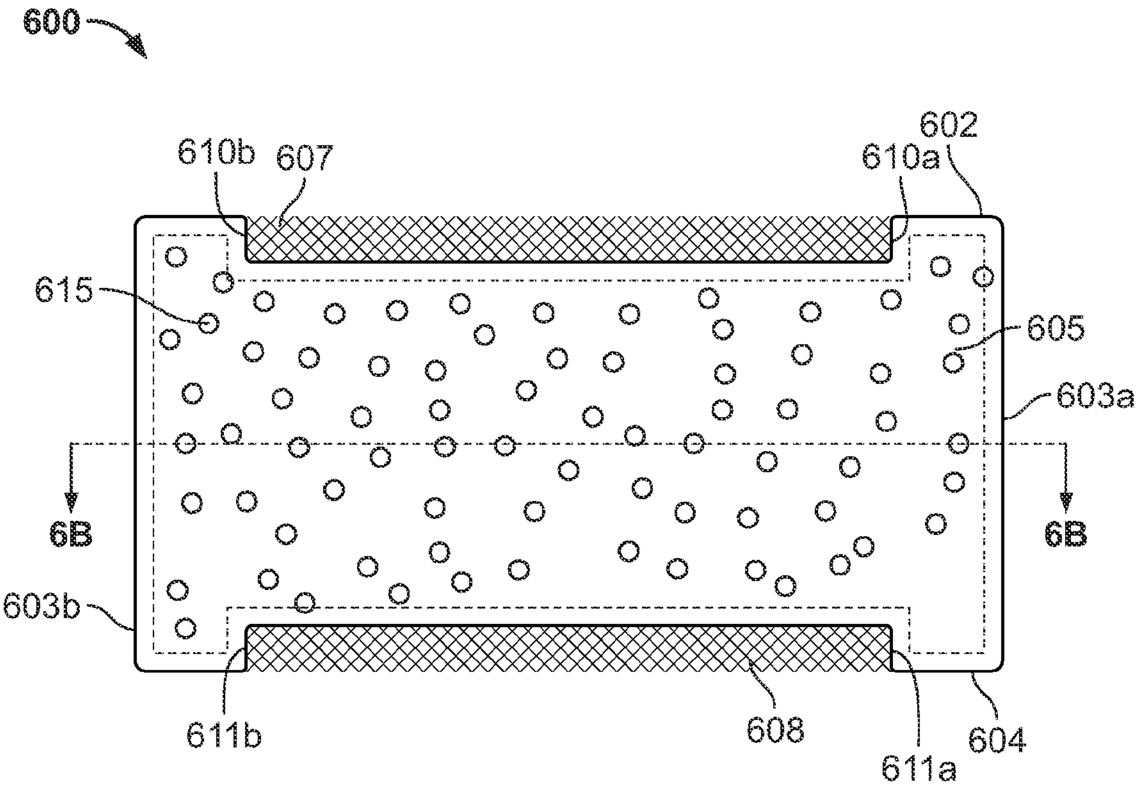
FIG. 6A-B are sectional views of a spinal implant according to an embodiment of the disclosure.
Figure 6B:
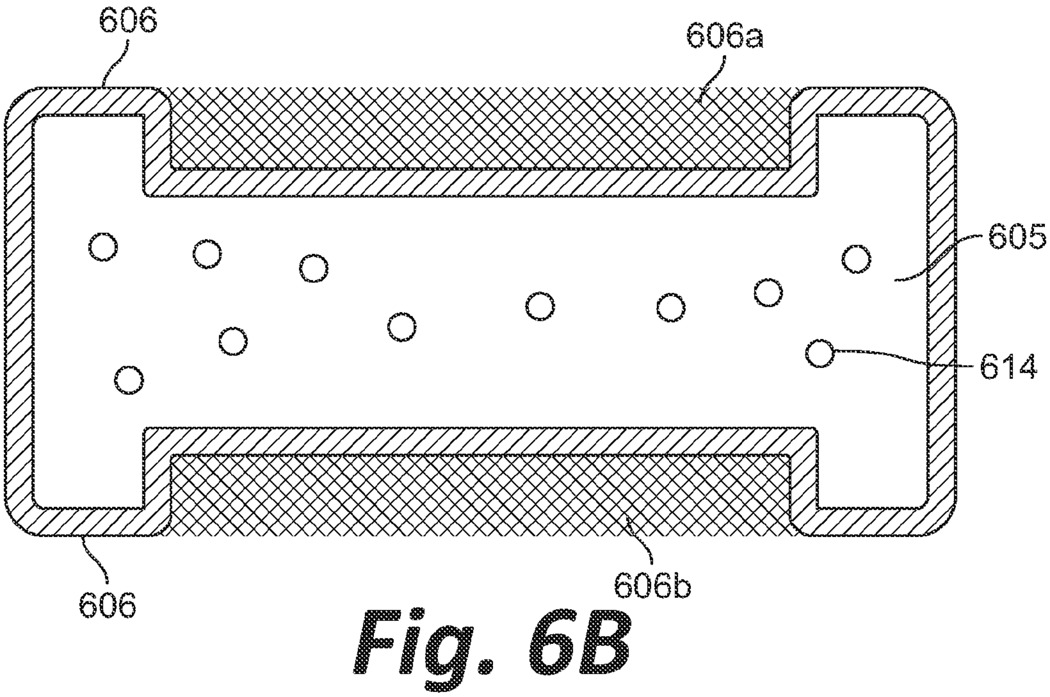

FIGS. 6A-B illustrate an implant 600 according to yet another embodiment of the disclosure. Unless otherwise stated, like reference numerals refer to like elements of above-described intervertebral implants 100, 200 and 300, but within the 600-series of numbers. Implant 600 includes a solid portion 605 and a porous portion 608 that forms a partial enclosure around solid portion 605, the porous portion including a superior porous portion 607, an inferior porous portion 608 and lateral porous portions 606*a*, 606*b*. Solid portion 605 has a first porosity, while the porous portions have a second porosity greater than the first porosity. Solid portion 605 has a superior surface 602, an inferior surface 604, and lateral surfaces 603*a*, 603*b*, both surfaces 603*a*, 603*b* extending the full height of implant 600. Solid portion 605 includes a recess on superior surface 602, which defines superior lip 610*a*, 610*b*. Superior porous portion 607 may be disposed within the recess formed along superior surface 602 of solid portion 605. Similar recesses are included around a full perimeter of implant 600. These include inferior surface 604 of solid portion 605 is a mirror image of superior surface 602 in that inferior surface 604 includes a recess defining inferior lips 611*a*, 611*b*. Inferior porous portion 608 may be disposed within the recess formed on inferior surface 604 of solid portion 605. In this manner, solid portion 605 may have an I-shape as illustrated in both sectional views illustrated in FIGS. 6A-B. Porous portions 607, 608 may be formed within the recesses of solid portion 605 so that a finished surface of implant 600 extending across the porous portion and the solid portion is flush. In other words, superior and inferior surfaces 602, 604 of implant 600 may be level along the length of implant 600 as the surfaces transition from superior and inferior surfaces 602, 604 of solid portion 605 to superior and inferior porous portions 607, 608, respectively.

FIG. 6B illustrates another sectional view of implant 600 taken along line 6B of FIG. 6A facing the inferior surface of the implant. In FIG. 6B, recesses in sides 606 of solid portion 605 are visible, as are lateral surface portions 606*a*, 606*b* disposed therein. Again, the porous portions may collectively extend around the implant in one continuous structure. Solid portion 605 may optionally include hollow channels 615 extending laterally through solid portion 605 and channels 614 extending in a superior-inferior direction through solid portion 605. The channels may be arranged in a grid formation spaced equal distances apart from each other or scattered in any suitable arrangement along the solid portion. Channels 614, 615 are cylindrical, but may be any suitable shape. The channels, whether laterally oriented or vertically oriented, may be positioned in the implant such that at least a portion of the channel extends through one or more of the porous portions. The channels may also be positioned in the implant so that at least a portion of the channel extends through the solid portion. Some channels may extend through both porous and solid portions of the implant. In some examples, the channels may extend at angles transverse to the surfaces of the implant or each other and may be nonlinear. The channels may also intersect with each other. It is also contemplated that the implant may include a graft window for added visibility.

Figure 7A:
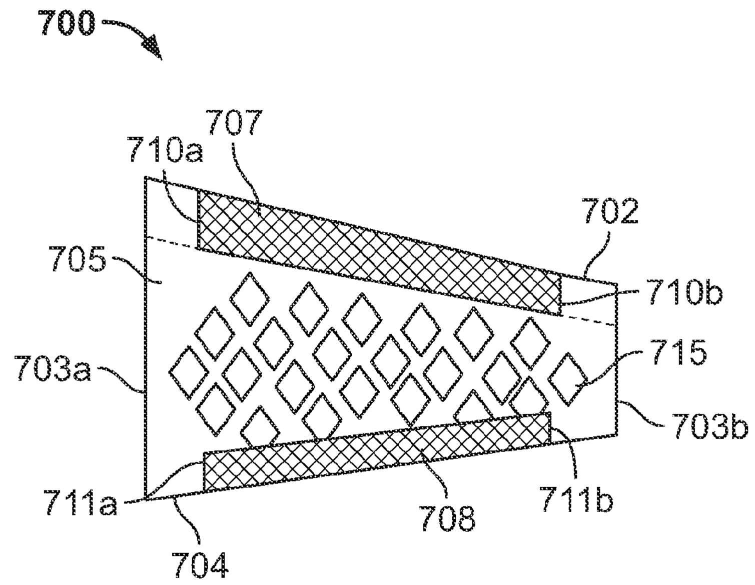
FIGS. 7A-B are side and top views, respectively, of a spinal implant according to an embodiment of the disclosure.
Figure 7B:
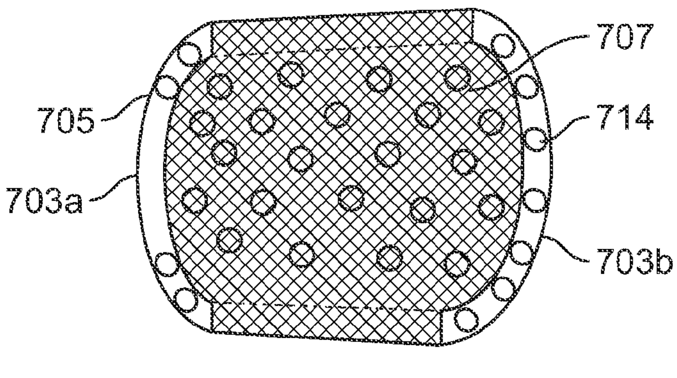

FIGS. 7A-B illustrate an implant 700 according to yet another embodiment of the disclosure. Unless otherwise stated, like reference numerals refer to like elements of above-described intervertebral implants 100, 200 and 300, but within the 700-series of numbers. Implant 700 includes a solid portion 705 having an anterior end 703*a* and a posterior end 703*b* with superior anterior lip 710*a*, superior posterior lip 710*b*, inferior anterior lip 711*a* and inferior posterior lip 711*b* that define recesses in superior and inferior surfaces 702, 704 of solid portion 705, respectively. The recesses formed in superior and inferior surfaces 702, 704 are filled by superior porous portion 707 and inferior porous portion 708, respectively. Porous portions 707, 708 may be formed within the recesses of solid portion 705 and result in a flush connection on an outer surface of implant 700. In other words, superior and inferior surfaces 702, 704 of implant 700 may be level along the length of implant 700 as the surfaces transition from superior and inferior surfaces 702, 704 of solid portion 605 to superior and inferior porous portions 707, 708, respectively. Superior and inferior surfaces 702, 704 of implant 700 may be at an angle with respect to one another. Thus, a height of anterior end 703*a* of implant 700 may be greater than the height of posterior end 703*b* of implant 700. Further, implant 700 may optionally include a plurality of channels 715 extending laterally through implant 700. Channels 715 may be hollow to promote visibility in radiological imaging. The porous portions are porous to further promote visibility and fusion with vertebral endplates, whereas the solid portion has nominal porosity. Solid portion 705 may also optionally include vertically oriented channels 714. Vertical channels 714 may be disposed adjacent to anterior and/or posterior ends 703*a*, 703*b* of solid portion 705 and extend between superior and inferior surfaces 702, 704 of solid portion 705. Vertical channels 714 may also be disposed within more medial locations within implant 700, and in such cases extend entirely through superior porous portion 707, solid portion 705 and inferior porous portion 708. Vertical channels 714 may intersect with lateral channels 715. Vertical channels 714 are cylindrical. Lateral channels 715 are diamond-shaped. It is contemplated that the vertical and/or lateral channels may have any suitable size or shape and may extend at various angles relative to the surfaces of the implant. The channels may also be nonlinear. The channels may be arranged in a grid formation spaced equal distances apart from each other or scattered in any suitable arrangement throughout implant 700. In some examples, an implant may only include channels in one direction through the implant.

Figure 8A:
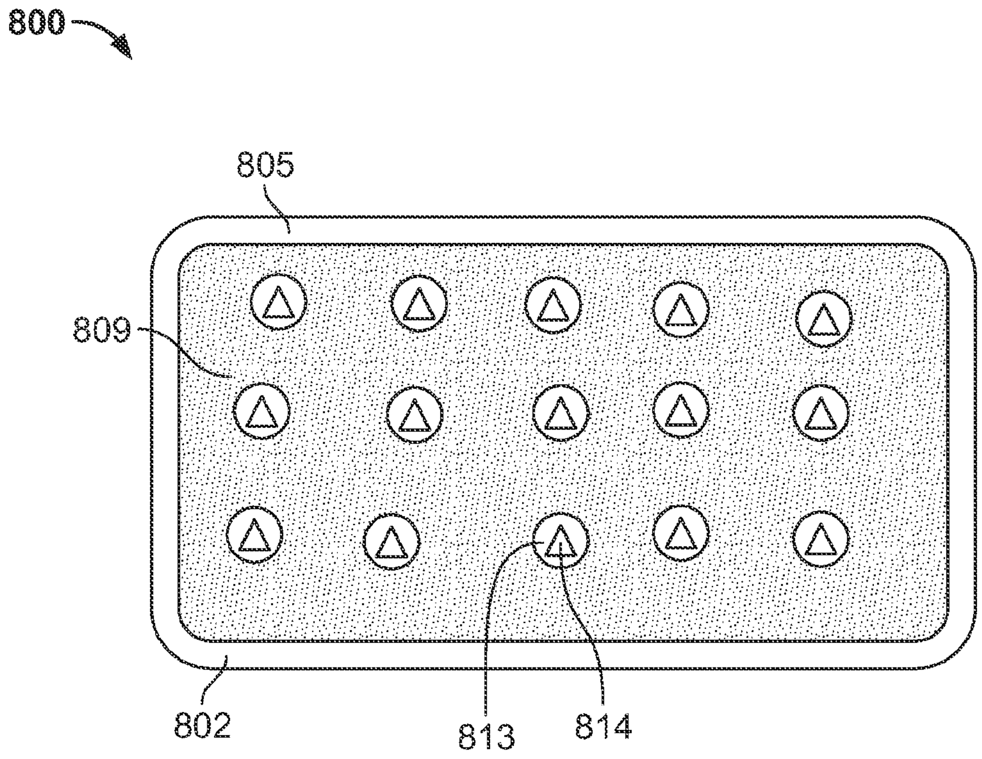
FIGS. 8A-B are top and side views, respectively, of a spinal implant according to an embodiment of the disclosure.
Figure 8B:
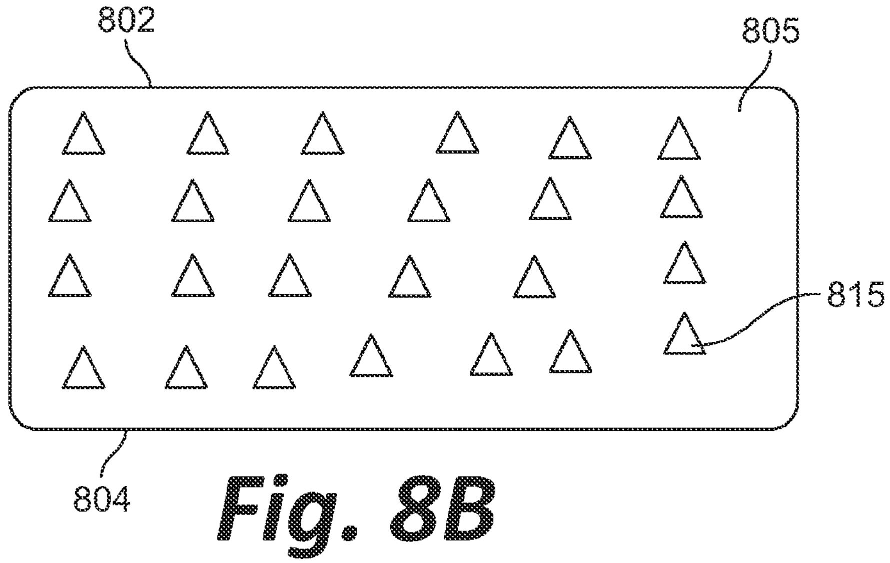

FIGS. 8A-B illustrate an implant 800 according to yet another embodiment of the disclosure. Unless otherwise stated, like reference numerals refer to like elements of above-described intervertebral implants 100, 200, 300 but within the 800-series of numbers. Implant 800 includes a porous portion 809, a peripheral portion 805 and solid tubular structures 813 defining channels 814 therein. As shown, implant 800 may be substantially rectangular in shape. Porous portion 809 is porous, whereas peripheral portion 805 is solid and has nominal porosity. Peripheral portion 805 may form an enclosure around porous portion 809. Tubular structures 813 may extend vertically through porous portion 809 between superior and inferior surfaces 802, 804 of implant 800. Tubular structures 813 may optionally define triangular channels 814 extending the full length of tubular structures 813. In the example of the embodiment shown, channels 814 are open. Additionally, FIG. 8B illustrates triangular channels 815 that extend laterally through implant 800. In some examples, lateral channels 815 may intersect with channels 814. Implant 800 may be varied in many ways. It is contemplated that the implant may include tubular structures that extend laterally through the solid portion and the porous portion. In some examples, tubular structures 813 and channels 814, 815 are arranged in a grid formation spaced evenly apart from each other, but the tubular structures and channels may be arranged in other patterns or random placements throughout the implant body. The tubular structures and channels may extend at various angles relative to the surfaces of the implant and may be nonlinear. In one example, an implant 800 may comprise an outer shell or peripheral portion 805, a fill material or porous portion 809 disposed within the outer shell 805, and a plurality of tubes or tubular structures 813 extending from a first outer surface of the implant 800 to a second outer surface of the implant 800 through the fill material 809, wherein the fill material 809 is more porous than the outer shell 805 and the plurality of tubes 813.

Figure 9A:
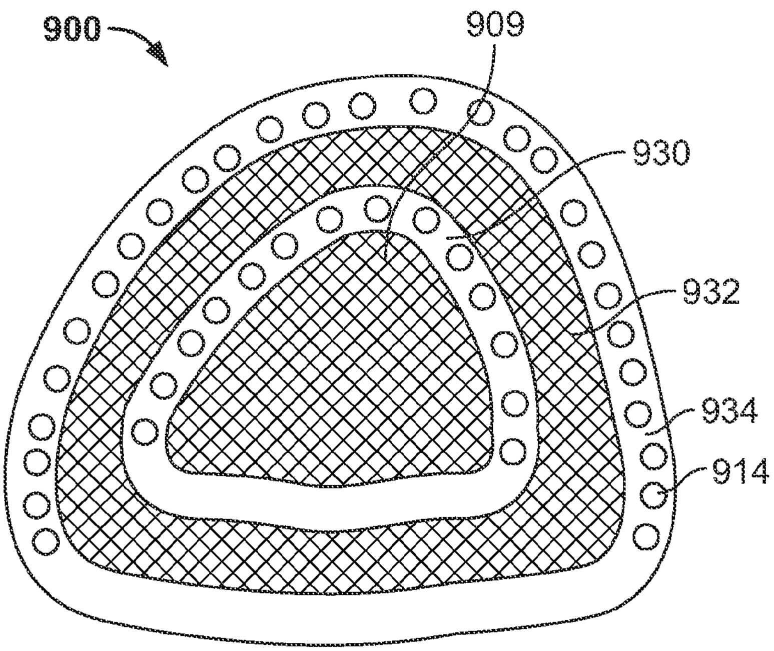
FIGS. 9A-B are top and side views, respectively, of a spinal implant according to an embodiment of the disclosure.
Figure 9B:
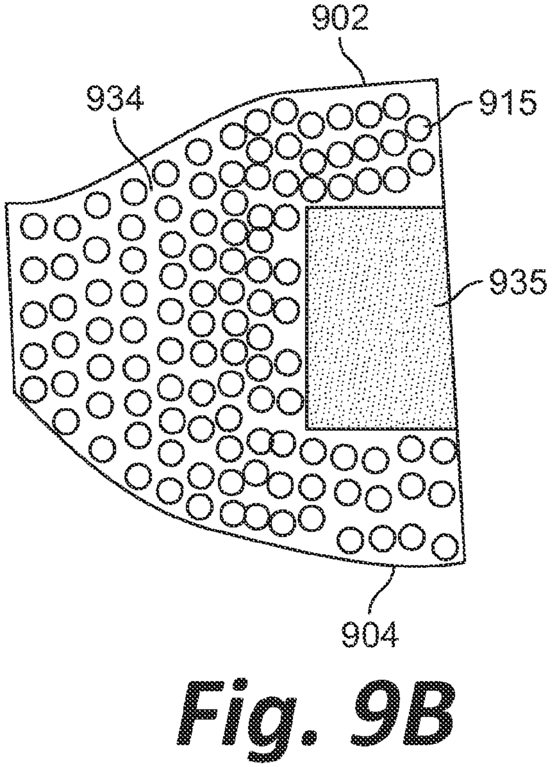

FIGS. 9A-B illustrate an implant 900 according to yet another embodiment of the disclosure. Unless otherwise stated, like reference numerals refer to like elements of above-described intervertebral implants 100, 200 and 300 but within the 900-series of numbers. As shown in FIG. 9A, implant 900 includes an inner porous portion 909 that has a first porosity. Inner porous portion 909 may be peripherally surrounded by an inner solid portion 930 with a nominal porosity much lower than the first porosity. Inner solid portion 930 may have an enclosed annular shape and include a plurality of vertical channels 914 extending therethrough between superior and inferior surfaces 902, 904 of implant 900. Inner solid portion 930 may be peripherally surrounded by outer porous portion 932, which has the first porosity. Outer porous portion may be peripherally surrounded by outer solid portion 934. Outer solid portion 934 may be substantially similar to inner solid portion 930 in that outer solid portion 934 is solid and includes vertical channels 914 disposed therein. The arrangement of the inner and outer solid portions promote the structural integrity of the implant while the porous portions promote bone ingrowth and visibility through the implant. Further, the channels in the inner and outer solid portions also promote visibility through the implant. Implant also includes lateral channels 915, shown in FIG. 9B, which extend from one lateral surface of implant 900 to the opposing lateral surface through outer solid portion 934, and may additionally extend through outer porous portion 932, inner solid portion 930 and inner porous portion 909 depending on the location of the channel. As shown in FIG. 9B, outer solid portion 934 may include an inserter attachment region 935 to attach an instrument to the implant for insertion of implant 900 into an intervertebral space. Such region 935 may be entirely solid without any channels therethrough. In one example, a spinal interbody implant 900 may comprise a core portion or inner solid portion 930 having a first porosity, the core portion 930 including a plurality of channels 914 extending from a first outer surface of the core portion 930 to a second outer surface of the core portion 930, a first material layer or outer porous portion 932 at least partially enclosing the core portion 930, the first material layer 932 having a second porosity greater than the first porosity, and a second material layer or outer solid portion 934 at least partially enclosing the first material layer 932, the second material layer 934 having a third porosity different from the second porosity.

Implant 900 may be varied in many ways. In some examples, the implant may have no vertical channels. Such an arrangement may provide additional structural strength relative to examples with vertical channels. Similarly, in some examples, the implant may have no lateral channels. It is also contemplated that the implant may include a lateral window defining a single bore larger than the channels to further enhance visibility. Vertical channels 914 and lateral channels 915 may intersect. It is contemplated that the inner and outer porous portions may also include vertical channels. The channels may be arranged in a grid formation and evenly spaced, or the channels may be more concentrated in some parts of the implant than others. The channels may extend at various angles transverse to the surfaces of the implant and may also be nonlinear.

Figure 10A:
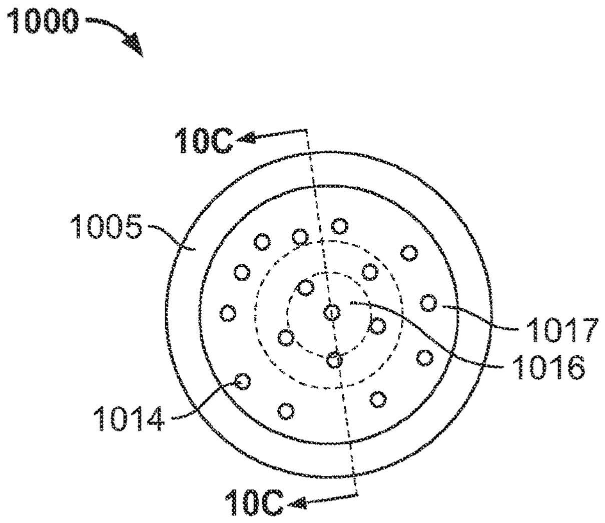
FIGS. 10A-C are top, side and cross-sectional views, respectively, of a spinal implant according to an embodiment of the disclosure.
Figure 10B:
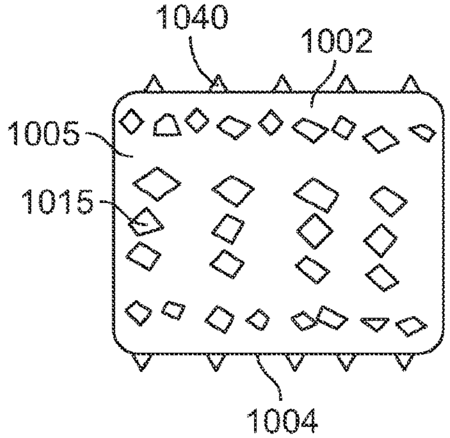
Figure 10C:
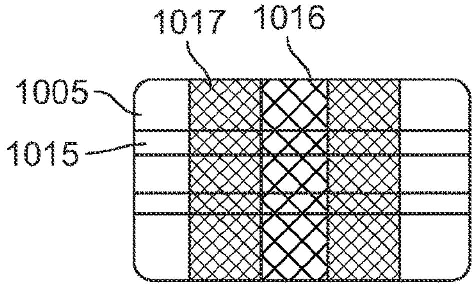

FIGS. 10A-C illustrate an implant 1000 according to yet another embodiment of the disclosure. Unless otherwise stated, like reference numerals refer to like elements of above-described intervertebral implants 100, 200 and 300 but within the 1000-series of numbers. Implant 1000 has an inner porous portion 1016, an outer porous portion 1017 and a peripheral portion 1005. The outer porous portion 1017 may be an annular layer that encloses the central inner porous portion 1016, while peripheral portion 1005 is a further annular layer that encloses outer porous portion 1017. The arrangement of these layers of implant 1000 are shown from above in FIG. 10A and in section in FIG. 10C. Inner porous portion 1016 has a first porosity, outer porous portion 1017 has a second porosity and peripheral portion 1005 has a third porosity. The first porosity may be greater than the second porosity and the second porosity may be greater than the third porosity. The third porosity is nominal or minimal, and the peripheral portion is effectively solid. In some examples, the radial inner portion has a porosity between 55-65% by volume and the radial outer portion has a porosity between 20-50% by volume.

Implant 1000 may optionally include vertical channels and lateral channels. Channels 1014 may extend between superior and inferior surfaces 1002, 1004 of implant 1000. Channels 1015 may extend from one lateral surface of implant 1000 to the opposing lateral surface. As shown, channels 1015 may only extend partially through implant 1000. In particular, the lateral channels may only extend through peripheral portion 1005 and not porous portions 1016, 1017. In some examples, the lateral channels may extend through both the peripheral and porous portions. In still further examples, the implant may have some lateral channels that extend through both the peripheral and porous portions, and other lateral channels disposed closer to the outer surfaces of the implant which only extend through the peripheral portion. In one arrangement, channels centrally located between the endplates extend through an entire width of the implant, while channels immediately adjacent to the endplates only extend through the solid peripheral portion. Further, outward facing superior and inferior surfaces 1002, 1004 of peripheral portion 1005 may optionally include teeth 1040 disposed thereon, as shown in FIG. 10B. When implant 1000 is positioned between vertebrae in a patient, teeth 1040 may grip vertebral endplates and anchor implant 1000 into an intervertebral space. As illustrated in FIG. 10B, teeth 1040 protrude from superior and inferior surfaces 1002, 1004 of peripheral portion 1005 to form a sharp segment for engagement with bone. In some examples, the teeth may be positioned on either or both of the porous outer surface and the solid outer surface of the implant. In one example, an implant 1000 may comprise an outer shell or peripheral portion 1005 including a first endplate surface or superior surface 1002 and a second endplate surface or inferior surface 1004, the first endplate surface 1002 and the second endplate surface 1004 being separated by a lateral wall of the outer shell 1005, a fill material disposed within the outer shell 1005, a first plurality of channels 1015 extending through the outer shell 1005 and the fill material with opposite ends at an outer surface of the lateral wall, the first plurality of channels 1015 being at a first distance from the first endplate surface 1002, and a second plurality of channels 1014 each having a length no greater than a thickness of the lateral wall, each of the second plurality of channels 1014 being at a second distance from the first endplate surface 1002, the second distance being less than the first distance, wherein the fill material is more porous than the outer shell 1005.

Figure 11A:
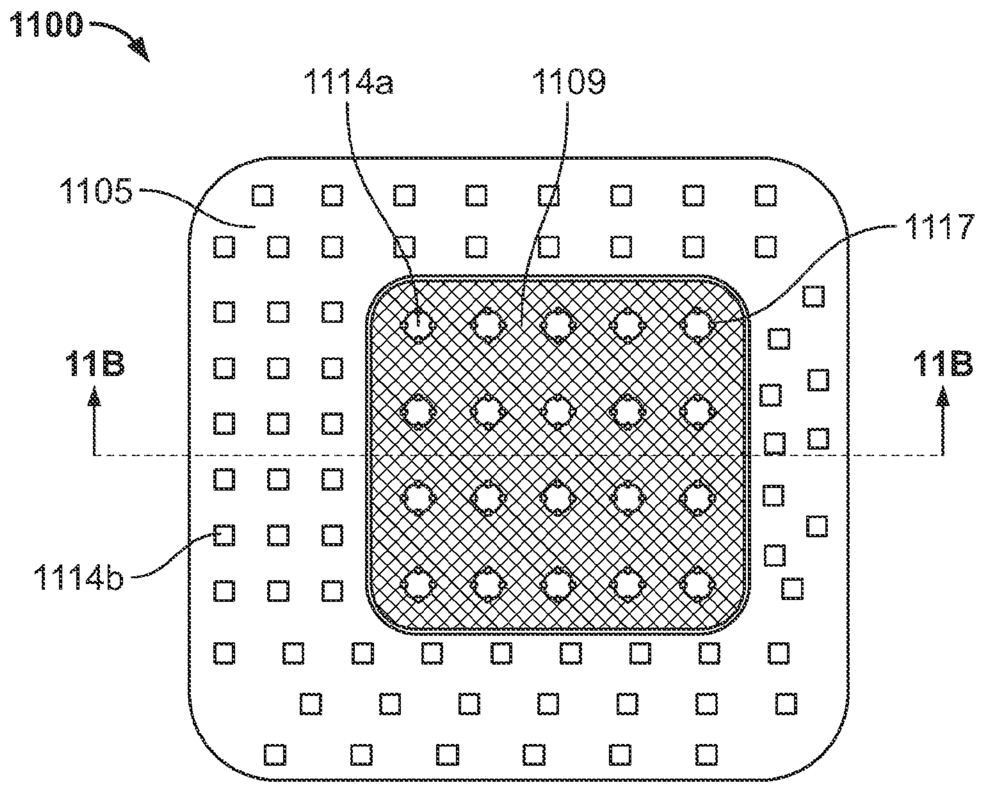
FIGS. 11A-B are top and sectional views, respectively, of a spinal implant according to an embodiment of the disclosure.
Figure 11B:
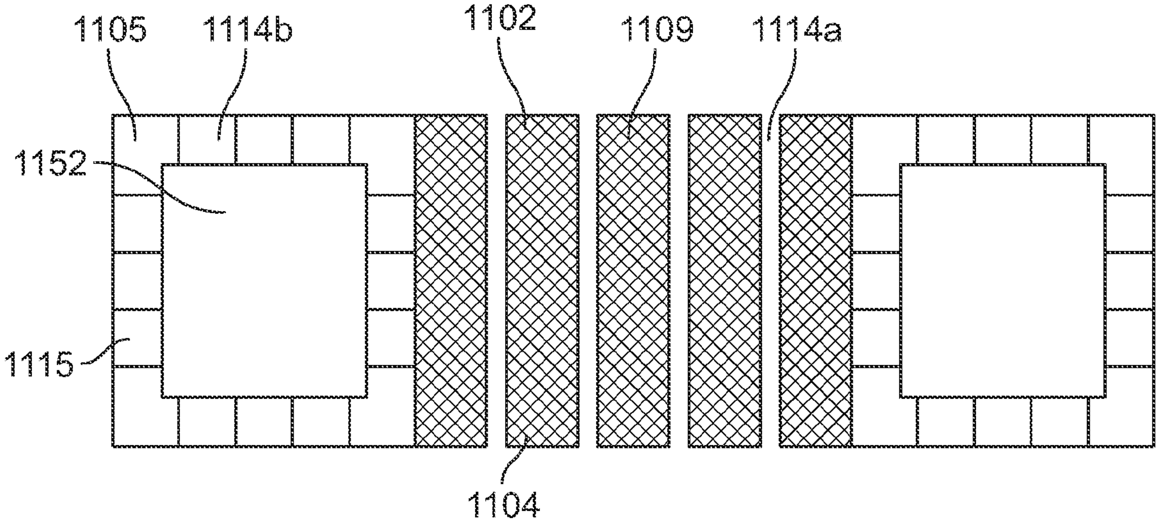

FIGS. 11A-B illustrate an implant 1100 according to yet another embodiment of the disclosure. Unless otherwise stated, like reference numerals refer to like elements of above-described intervertebral implants 100, 200 and 300 but within the 1100-series of numbers. Implant 1100 includes a porous portion 1109 and a peripheral portion 1105 peripherally surrounding the porous portion 1109. Porous portion 1109 is porous whereas peripheral portion 1105 is solid with nominal porosity. Porous portion 1109 may optionally include channels 1114*a* extending vertically through porous portion 1109 between superior and inferior surfaces 1102, 1104 of implant 1100, as shown in FIGS. 11A-B. Channels 1114*a* may be arranged in a grid pattern spaced at equal distances from each other. Each channel 1114*a* may be hollow and include five struts 1117 disposed around the circumference of channel 1114*a* extending the length of channel 1114*a*. Struts 1117, best shown in FIG. 11A, may be solid and provide structural reinforcement to hollow channels 1114*a* within porous portion 1109. In some examples, four struts are included surrounding a single channel. In other examples, a different quantity of struts may be included. Each strut 1117 may taper toward an outer surface of the implant, providing greater surface area contact with porous portion through the gaps between adjacent struts 1117. In some examples, some or all of the struts have no tapered ends. Additionally, through peripheral portion 1105 are additional channels 1114*b*. As shown, these channels may have a different shape compared to channels 1114*a*. As shown in FIG. 11B, peripheral portion 1105 may optionally include a void 1152 between the superior and inferior surfaces of peripheral portion 1105, which may promote improved imaging characteristics of implant 1100. Thus, some channels 1114*b* may extend through peripheral portion 1105 between superior surface 1102 and void 1152, while other channels 1114*b* extend between void 1152 and inferior surface 1104. And, lateral channels 1115 may also be included, shown in FIG. 11B. These channels only extend through peripheral portion 1105. It is contemplated that any individual or group of the channels may be arranged in any formation, oriented in any direction, and shaped and sized in any suitable manner. It is also contemplated that the channels may include any number of struts surrounding the channels, such as, e.g., four, five or six struts evenly distributed around the circumference of the channels. The struts need not be evenly spaced around the channels.

Figure 12A:
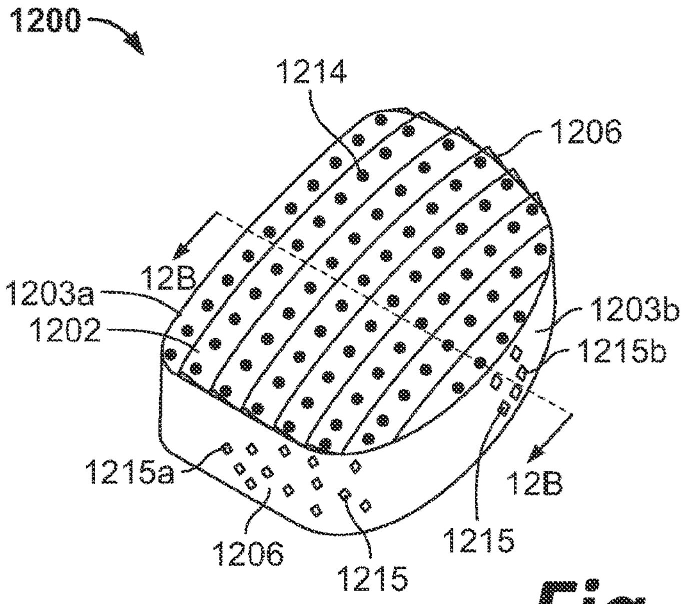
FIGS. 12A-B are perspective and sectional views, respectively, of a spinal implant according to an embodiment of the disclosure.
Figure 12B:
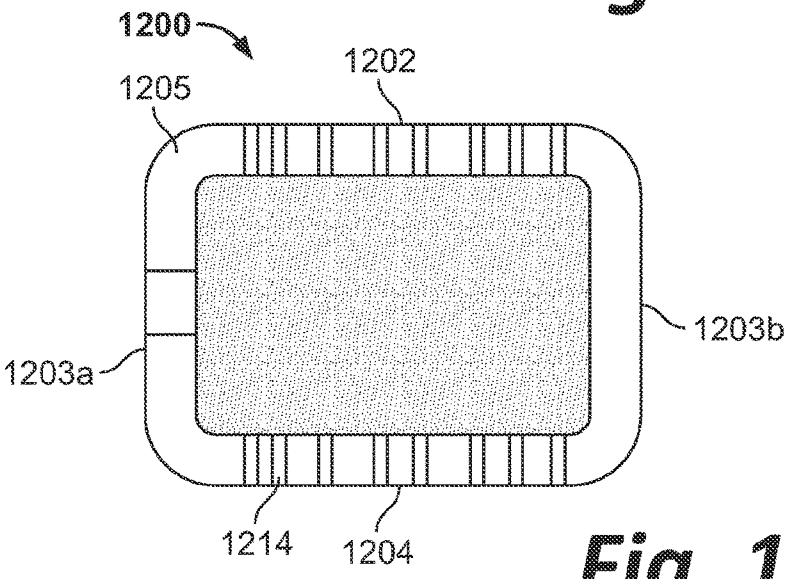

FIGS. 12A-B illustrate an implant 1200 according to yet another embodiment of the disclosure. The section 12B indicated in FIG. 12A is shown in FIG. 12B. Unless otherwise stated, like reference numerals refer to like elements of above-described intervertebral implants 100, 200 and 300 but within the 1200-series of numbers. Implant 1200 includes a superior surface 1202, an inferior surface 1204, a first side 1203*a*, a second side 1203*b* and lateral ends 1206. As illustrated in FIG. 12B, implant 1200 includes a porous portion 1209 and a peripheral portion 1205 that fully encloses porous portion 1209. Porous portion 1209 is porous and peripheral portion 1205 is solid in that its porosity is nominal. Implant 1200 may optionally include diamond-shaped lateral channels 1215 through peripheral portion. A first set of channels 1215A may extend inward from lateral surfaces 1206, while a second set of channels 1215B may extend inward from surfaces 1203*a* and 1203*b* of implant 1200. As shown in FIG. 12A, surfaces 1206 are opposite one another while surfaces 1203*a* and 1203*b* are also generally opposite one another. Both sets of channels 1215*a*, 1215*b* may extend through peripheral portion 1205, but not porous portion 1209. It is contemplated that the channels may also have a circular or other suitable shape such as a square, triangle, etc. Implant 1200 also includes vertical channels 1214 distributed across the implant body and extending through the peripheral portion 1205 but not the porous portion 1209, as best shown in FIG. 12B.

Figure 13:
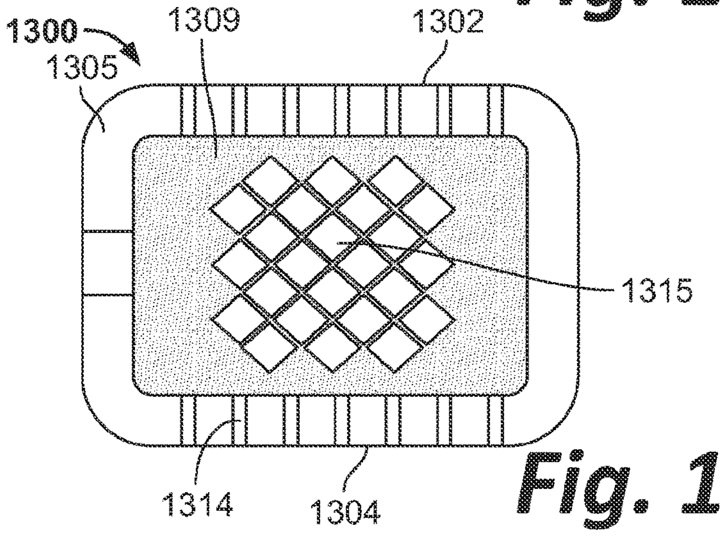
FIG. 13 is a sectional view of a spinal implant according to an embodiment of the disclosure.

FIG. 13 illustrates an implant 1300 according to yet another embodiment of the disclosure. FIG. 13 depicts a cross-sectional view based on a section cut similar to FIG. 12B. Unless otherwise stated, like reference numerals refer to like elements of above-described intervertebral implants 100, 200 and 300 but within the 1300-series of numbers. Implant 1300 has a structure similar to implant 1200 shown in FIGS. 12A-B, although lateral channels 1315 may optionally extend through porous portion 1309 in addition to peripheral portion 1305. Channels 1315 may be open between opposite ends of the implant. Similar to implant 1200 in FIGS. 12A-B, vertical channels 1314 may extend through peripheral portion 1305 but not porous portion 1309. However, in some examples, one or more channels 1314 may extend continuously between the superior and inferior surfaces of the implant. In some examples, one or more of channels 1315 may intersect with one or more of channels 1314. And, in further examples, one or more of channels 1314, 1315 may be filled with porous material.

Figure 14:
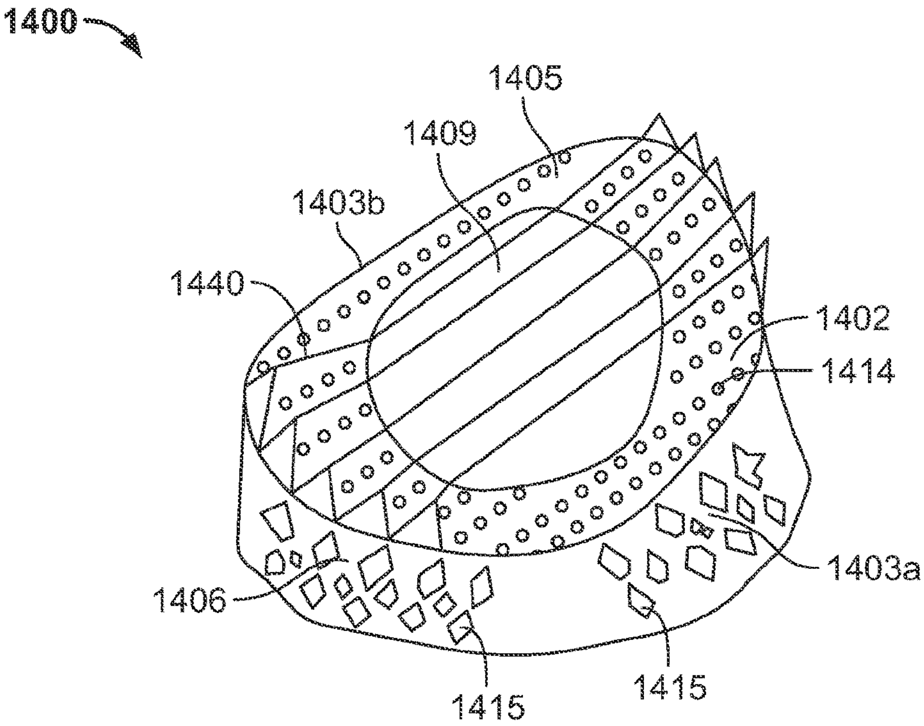
FIG. 14 is a perspective view of a spinal implant according to an embodiment of the disclosure.

FIG. 14 illustrates an implant 1400 according to yet another embodiment of the disclosure. Unless otherwise stated, like reference numerals refer to like elements of above-described intervertebral implant 1200, but within the 1400-series of numbers. Implant 1400 includes a porous portion 1409 and a peripheral portion 1405 peripherally surrounding porous portion 1409. Porous portion 1409 and peripheral portion 1405 may optionally include both lateral channels 1415 and vertical channels 1414 in the manner contemplated for implant 1200 and shown in FIGS. 12A-B. Superior surface 1402 of implant 1400 may optionally include a plurality of teeth 1440 on one or both of a superior surface 1402 and inferior surface of implant 1400. The teeth each may extend across a width of the implant over both a surface of peripheral portion 1405 and porous portion 1409. In some examples, teeth 1440 have a length that extends from lateral edge 1406 of peripheral portion 1405 to the inner circumference of peripheral portion adjacent porous portion 1409 along superior surface 1402. The teeth enhance the grip and anchorage of the implant when the implant is positioned in an intervertebral space. Although not shown, it is contemplated that the inferior surface may include the same toothed arrangement as the superior surface. It is also contemplated that the superior surface of the implant may include anywhere between one tooth and any number of teeth sufficient to span a majority of the superior surface of the implant. The teeth may vary in height, sharpness of the peak edge and distance between each tooth. The teeth may alternatively extend across the superior surface from the anterior edge to the posterior edge of the implant, or at any orientation that is at an angle relative to that illustrated. In some examples, the teeth may be jagged or wavy rather than straight.

Figure 15:
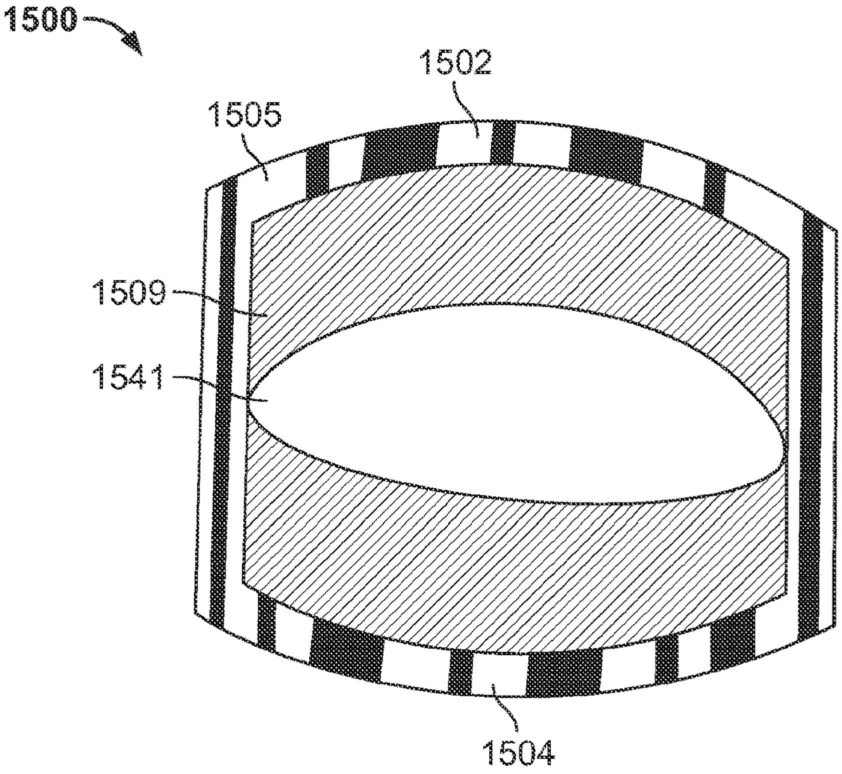
FIG. 15 is a cross-sectional view of a spinal implant according to an embodiment of the disclosure.

FIG. 15 illustrates an implant 1500 according to yet another embodiment of the disclosure. Unless otherwise stated, like reference numerals refer to like elements of above-described intervertebral implants 100, 200 and 300, but within the 1500-series of numbers. Implant 1500 includes a porous portion 1509 and a solid peripheral portion 1505 surrounding porous portion 1509. Implant 1500 may optionally include channels as contemplated for implants 1200, 1300, 1400. Further, implant 1500 may have elastic deformation properties. In particular, implant 1500 includes superior surface 1502 and inferior surface 1504 which, when implant is positioned in a disc space of the spine, contact adjacent vertebral bodies. Load from the vertebral bodies applies pressure to the superior and inferior surfaces 1502, 1504 and causes a shape of the implant to change. Load may be from movement of the spine, the weight of the spine, or other loads distributed through the spine. Such deformation of the implant is made possible through a void 1541 within porous portion 1509. Void 1541 has a first volume when no load is applied to the implant, and has a second volume lower than the first volume once load is applied, as it becomes smaller. Void 1541 has a size larger than, e.g., channels described in other embodiments throughout this disclosure which results in less material of implant 1500 surrounding void 1541 compared to an implant with channels instead of a void. The size of void 1541 results in implant 1500 having a reduced rigidity relative to an implant lacking a single void of such size (e.g., an implant having channels or no spaces at all), which allows the shape of implant 1500 to adjust under certain loads or pressures. Because of the void, the implant has room to compress without damage being caused to the structural components of implant 1500. When load is removed from the implant, implant 1500 will return to its previous shape prior to being subject to load, i.e., a resting state position. In one example, the load is in the form of compression between the vertebral bodies adjacent implant 1500. One advantage of implant 1500 is that it is adaptive to real time conditions in the spine and may obtain an ideal fit in a disc space even when it may not be ideally shaped in an unloaded condition. Additionally, the flexibility of implant 1500 improves mobility of the spine. In one example, a spinal interbody implant 1500 may comprise an outer shell or peripheral portion 1505 including a plurality of openings therein, and a fill material or porous portion 1509 disposed in the outer shell 1505, the fill material 1509 having a void 1541 therein, wherein the outer shell 1505 is deformable as a function of a force applies to an outer surface 1502, 1504 of the outer shell 1505 such that an increase in the force coincides with a decrease in a volume of the void, and wherein the fill material 1509 is more porous than the outer shell 1505.

Figure 16A:
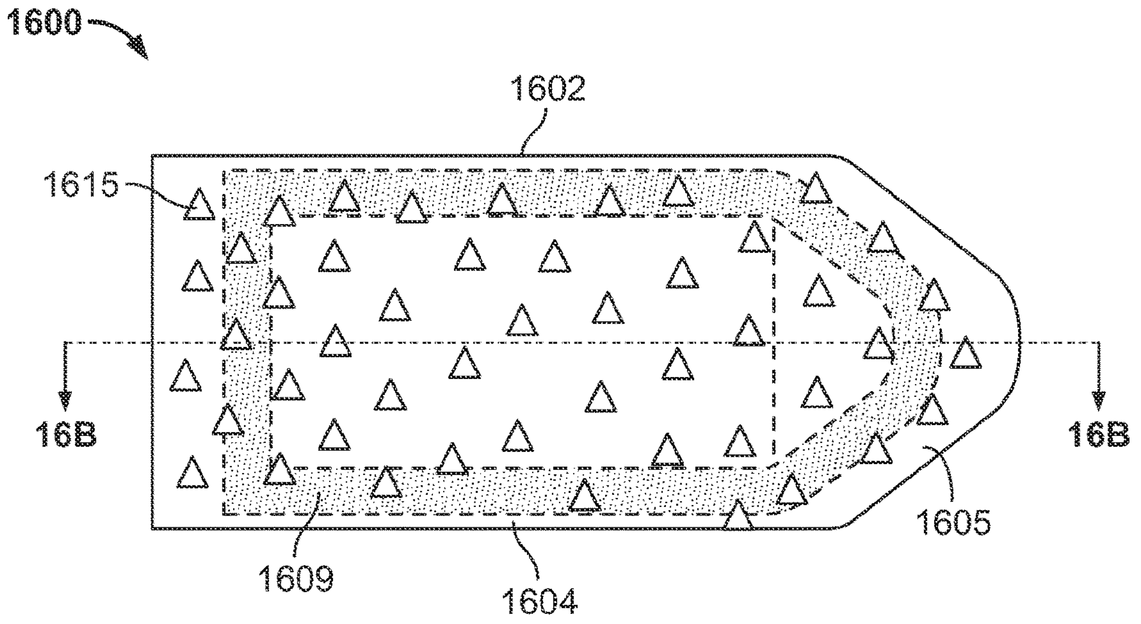
FIG. 16A-B are side and sectional views, respectively, of a spinal implant according to an embodiment of the disclosure.
Figure 16B:
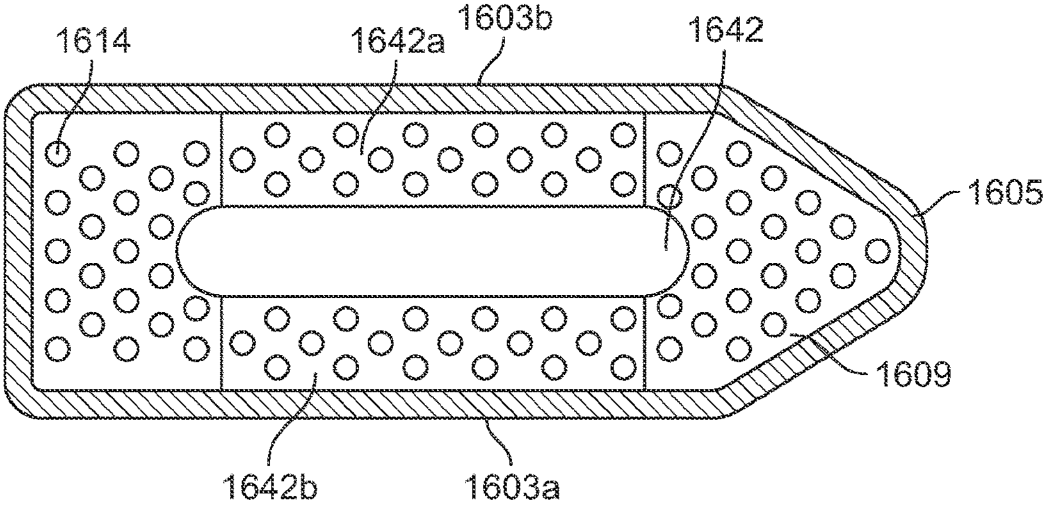

FIGS. 16A-B illustrate an implant 1600 according to yet another embodiment of the disclosure, in which FIG. 16A is a side view and FIG. 16B is a top down cross-sectional view along axis 16B of FIG. 16A. Unless otherwise stated, like reference numerals refer to like elements of above-described intervertebral implants 100, 200 and 300, but within the 1600-series of numbers. Implant 1600 includes a porous portion 1609 and a solid peripheral portion 1605 peripherally wrapped around porous portion 1609 as shown in FIGS. 16A and 16B. Implant 1600 may optionally include a graft window 1642 disposed through a central region of the implant from superior surface 1602 to inferior surface 1604. As shown in FIG. 16B, implant 1600 may also optionally include radiolucent windows 1642*a*, 1642*b* adjacent to graft window 1642. The graft window and radiolucent windows provide improved radiolucency of the implant. Although a majority of porous portion 1609 lies within an inner surface of peripheral portion 1605, peripheral portion 1605 may optionally include openings on lateral sides that are best shown in FIG. 16B. The openings may be absent the porous material included in porous portion 1609. Implant 1600 may optionally include vertical channels 1614 shown in FIG. 16B, the channels 1614 extending from superior surface 1602 to inferior surface 1604. Channels 1614 are disposed through both porous portion 1609 and peripheral portion 1605. Implant 1600 may optionally include channels 1615 extending in a lateral direction through the openings described above. In some examples, one or more channels 1615 extend between end surface 1603*a* and end surface 1603*b* only through peripheral portion 1605. In some examples, one or more channels 1615 extend between end surface 1603*a* and end surface 1603*b* through peripheral portion 1605 and porous portion 1609. In some examples, one or more channels 1615 extend from end surface 1603*a* to one side of graft window 1642 through peripheral portion 1605 and porous portion 1609, and then continue on the other side of graft window 1642 extending to end surface 1603*b* along the same axis. It is contemplated that in some examples, the channels may be randomly distributed around the implant and may be oriented so that one or more channels is oriented at a different trajectory than one or more of the other channels.

Figure 17A:
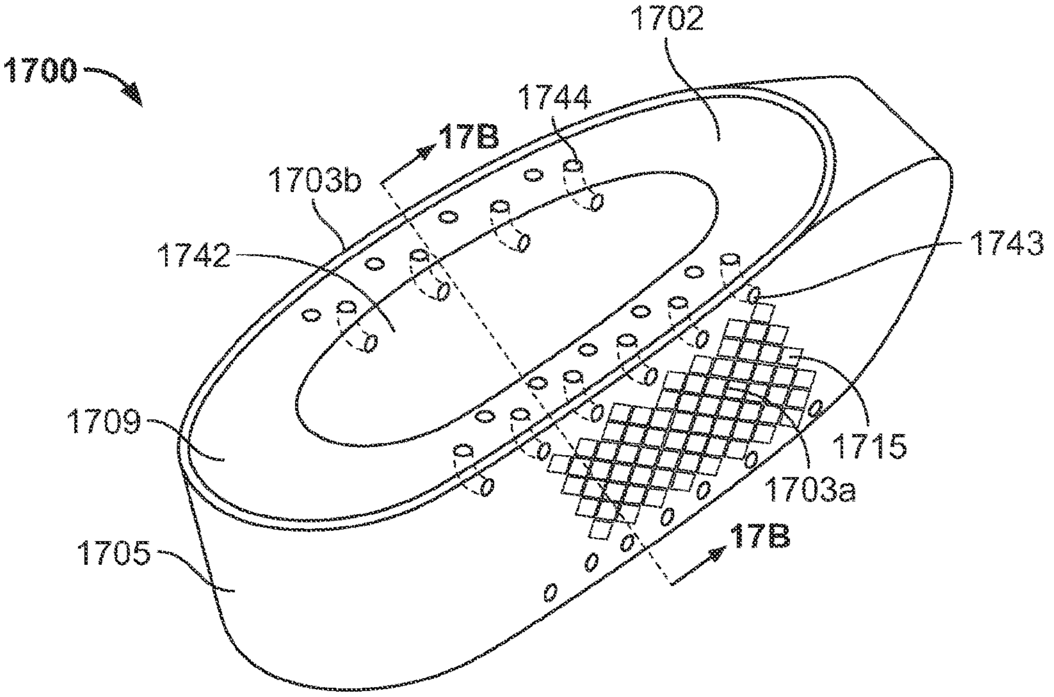
FIGS. 17A-B are perspective and sectional views, respectively, of a spinal implant according to an embodiment of the disclosure.
Figure 17B:
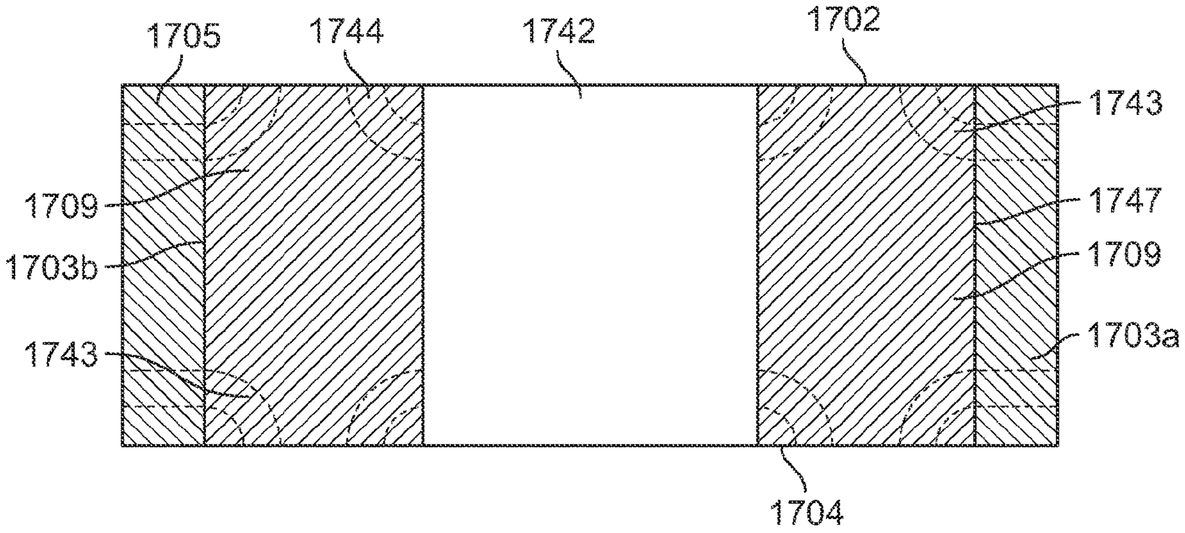

FIGS. 17A-B illustrate an implant 1700 according to yet another embodiment of the disclosure. Unless otherwise stated, like reference numerals refer to like elements of above-described intervertebral implants 100, 200, 300, but within the 1700-series of numbers. Implant 1700 includes a porous portion 1709 and a solid peripheral portion 1705 peripherally enclosing porous portion 1709. Porous portion 1709 encloses a graft window 1742 as shown in FIGS. 17A-B that extends from superior surface 1702 of porous portion 1709 to inferior surface 1704 of porous portion 1709. Peripheral portion 1705 may optionally include an array of diamond-shaped channels 1715 extending through a side of the implant. Channels 1715 may extend through peripheral portion 1705 and porous portion 1709. Channels similar to channels 1715 may be included on an opposing side of the implant across graft window 1742. In one example, a spinal interbody implant 1700 may comprise an outer portion or peripheral portion 1705 forming a first part of a top surface or superior surface 1702 of the implant 1700, an inner portion or porous portion 1709 disposed within the outer portion 1705, the inner portion 1709 forming a second part of the top surface 1702 of the implant 1700, and a first channel or inner fusion path 1743 extending through the outer portion 1705 and the inner portion 1709, a first end of the channel 1743 being on a lateral surface of the implant and a second end of the first channel 1743 opposite the first end being on the top surface 1702 or a bottom surface or inferior surface 1704 of the implant 1700, wherein the inner portion 1709 is more porous than the outer portion 1705.

Implant 1700 may optionally include outer and inner fusion paths 1743, 1744, respectively, defined by a plurality of curved bores connecting one of a superior or inferior surface of the implant with an outer or inner side surface of the implant, as best shown in FIG. 17B. Outer fusion paths 1743 may extend from an outer side surface of the implant to a superior or inferior surface, while inner fusion paths 1744 may extend from an inner side surface of the implant to a superior or inferior surface. Depicted in FIG. 17B, outer fusion paths 1743 may be disposed between two surfaces of porous portion 1709 adjacent the corner where the two surfaces intersect. For example, outer fusion paths 1743 are disposed between superior surface 1702 of porous portion 1709 and an outer side surface 1747 of implant 1700. As described above, outer fusion paths 1743 may be disposed between superior surface 1702 and outer side surface 1747. Inner fusion paths 1744 may be disposed between superior surface 1702 and graft window 1742. Outer fusion paths 1743 may also be disposed between inferior surface 1704 of porous portion 1709 and outer side surface of implant 1700. Inner fusion paths 1744 may also be disposed between inferior surface 1704 and graft window 1742. Opposing sides of graft window 1742 may be mirror images of each other, including the same layout of fusion paths 1743, 1744. In some examples, fusion paths 1743, 1744 are disposed in a pattern evenly apart from each other along the length of the implant. It is further contemplated that the fusion paths may extend any length through any section of the implant. The quantity of fusion paths within the implant may be greater or fewer than that shown in FIG. 17A. Additionally, the implant may include greater or fewer lateral channels. The channels may be oriented in transverse directions, such as a lateral direction. The channels may be nonlinear or may be unevenly distributed on each lateral side of the graft window. The channels may intersect with the fusion paths. In an alternative arrangement, implant 1700 may have fill throughout its interior so that there is no graft window. In such cases, fusion paths may be only externally facing.

Fusion paths allow for accelerated integration and fixation of the implant into the vertebral space. Bone is known to grow multidirectional and high areas of fusion are the graft window and outside profile of the implant because those areas are packed with biologics. Bone growth from the endplate may connect with bone growth in the graft window to create an anchor that holds the implant in place, ensuring fusion continues. This is advantageous over completely vertical channels in that the shorter distance for bone growth to travel through the fusion paths of implant 1700 results in a shorter time required for regrowth post-surgery.

Figure 18A:
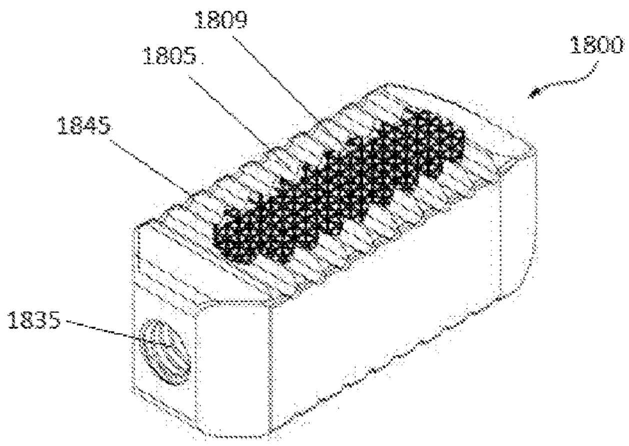
FIGS. 18A-B are perspective and exploded views, respectively, of a spinal implant according to an embodiment of the disclosure.
Figure 18B:
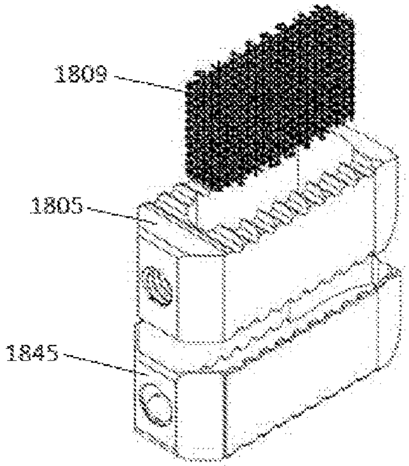

FIGS. 18A-B illustrates an implant 1800 according to yet another embodiment of the disclosure. Implant 1800 includes a core 1809, a shell 1805 peripherally wrapped around core 1809 and a jacket 1845 peripherally wrapped around shell 1805. Each component is visibly shown in the exploded view of implant 1800 in FIG. 18B. Jacket 1845 and core 1809 may have a polymer matrix with a metal distributed throughout the matrix, while shell 1805 may be a polymer. Core 1809 may be porous. In one specific example, the jacket and core include titanium for the metal component. The polymer shell provides radiolucency for implant 1800. In some examples, jacket 1845 may be a polymer, core 1809 may be a metal, and shell 1805 may include a polymer matrix with a metal distributed throughout the matrix. Implant 1800 may optionally include an attachment port 1835 configured to receive an insertion instrument for insertion into an intervertebral space. In some examples, implant 1800 may be additively manufactured inclusive of core 1809, shell 1805 and jacket 1845. In one example, a spinal interbody implant 1800 may comprise a core portion or core 1809 including a first material and a second material different from the first material, the first material having a first porosity, an inner peripheral portion or shell 1805 enveloping the core portion 1809, the inner peripheral portion 1805 including a third material and having a second porosity less than the first porosity, and an outer peripheral portion or jacket 1845 enveloping the inner peripheral portion 1805, the outer peripheral portion 1845 including a fourth material and a fifth material.

Figure 19:
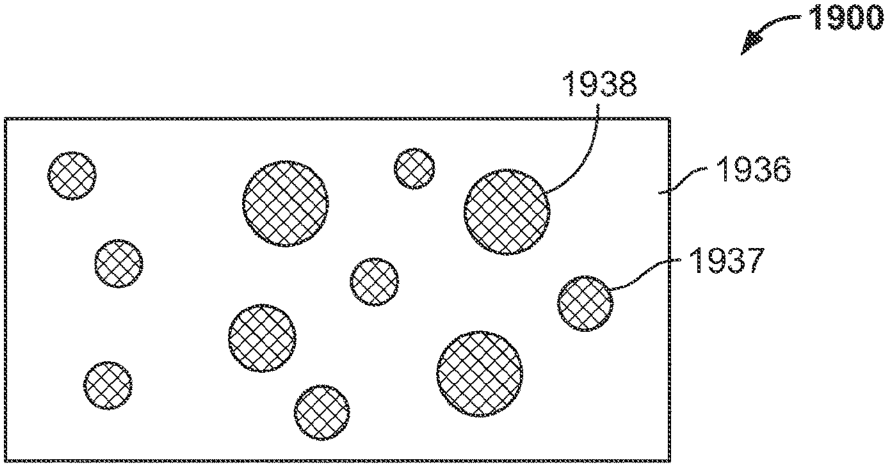
FIG. 19 is a schematic view of a material combination usable to form a spinal implant.

FIG. 19 illustrates a composite material 1900 that may be used to form part or all of a spinal interbody implant. In some examples, composite material 1900 may be used for one or more of the jacket 1845 and core 1809 portions of implant 1800. Composite material 1900 may include a polymer matrix 1936 with particles of a first material 1937 and particles of a second material 1938 distributed therein. In some examples, polymer 1936 may be polyether-ether ketone (PEEK). In some examples, first material 1937 may be titanium. In some examples, second material 1938 may be bioglass or hydroxyapatite. Alternatively, in some embodiments, it is contemplated that composite material 1900 may include a temporary material along with other non-temporary materials such that the temporary material is dissolved as part of the implant manufacturing process to leave a porous structure that includes the non-temporary materials. Examples of some dissolvable materials are provided elsewhere in the disclosure. This configuration of the composite material may promote osteogenesis by, over time, providing voids for bone to grow into. In one example, a spinal interbody implant 1900 may comprise a body including a polymer matrix 1936, a first material 1937 and a second material 1938, the first material 1937 and the second material 1938 being distributed throughout the polymer matrix 1936, wherein the first material 1937 is titanium, and wherein the second material 1938 is bioglass or hydroxyapatite.

Figure 20A:
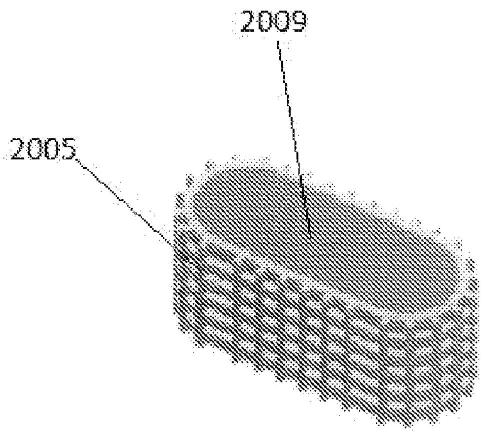
FIG. 20A is a perspective view of a spinal implant component according to an embodiment of the disclosure.
Figure 20B:
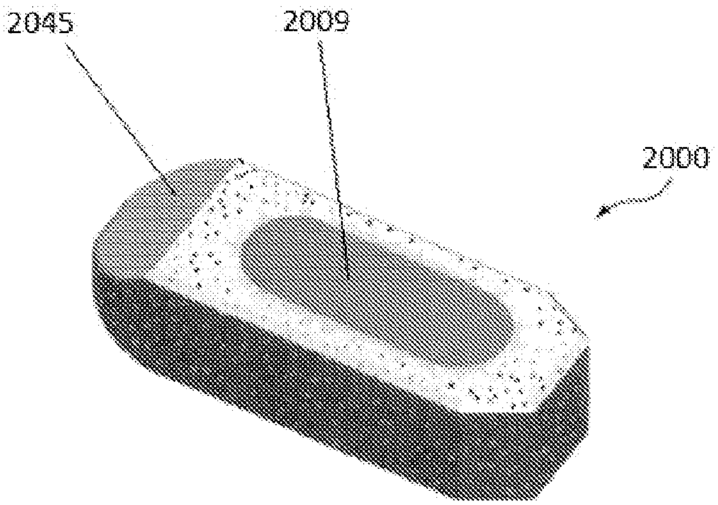
FIG. 20B is a perspective view of a fully formed spinal implant inclusive of the component shown in FIG. 20A.

FIGS. 20A-B illustrate an implant 2000 according to yet another embodiment of the disclosure. Implant 2000 includes a core 2009 peripherally surrounded by a scaffold 2005. Core 2009 may be porous whereas scaffold 2005 is solid. FIG. 20A illustrates core 2009 surrounded by scaffold 2005. FIG. 20B illustrates implant 2000 further including a sheath 2045 compression molded to scaffold 2005. Sheath 2045 may be additively manufactured around core 2009 and scaffold 2005. Sheath 2045 comprises a polymer matrix with metal particles, e.g., titanium, distributed and embedded throughout the polymer matrix of sheath 2045, similar to the embodiment described above with reference to FIG. 19. In some examples, the superior and inferior surfaces of the core may be sealed to prevent the sheath from interfacing with the core.

Figure 21A:
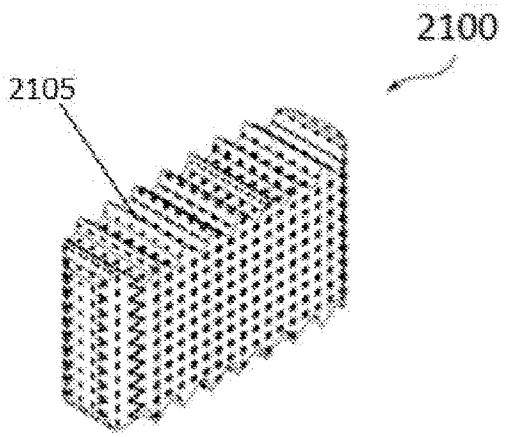
FIG. 21A is a perspective view of a spinal implant according to an embodiment of the disclosure.
Figure 21B:
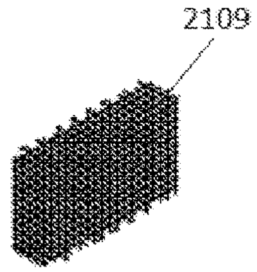
FIG. 21B is a core disposed entirely within the spinal implant of FIG. 21A.

FIGS. 21A-B illustrate an implant 2100 according to yet another embodiment of the disclosure. Implant 2100 includes a core portion 2109 and a shell 2105 that fully encloses core portion 2109. Assembled implant 2100 is depicted in FIG. 21A with the core portion disposed inside shell 2105. Core portion 2109 is depicted in FIG. 21B. Core portion 2109 may be formed of a porous dissolvable material and is shown in a pre-dissolved state in FIG. 21B. Shell 2105 may be a polymer matrix with metallic particles distributed and embedded therein. The metallic particles may be titanium or any other suitable metal for forming the shell. It is also contemplated that the shell may be porous. The implant may be designed so that after the implant is fully assembled with the shell formed around the core portion, the dissolvable material of the core portion is dissolved leaving behind the shell with a hollow interior in place of the core portion. In some examples, the core portion may be formed of a material that dissolves using a liquid solution, e.g., salt dissolved in an aqueous solution. In these examples, the implant 2100 may be inserted into and/or surrounded by a liquid until the core portion fully dissolves, then removed from the liquid leaving behind a shell with a hollow interior. In other examples, the core portion (e.g., 2109) may be formed of a polymer coated with a thin metal layer such that when the core portion is heated to a temperature above the melting point of the polymer in the core portion but below the melting point of the polymer compound from which the shell (e.g., 2105) is formed, the polymer of the core portion dissolves. In one example, the core may be formed of a polyurethane coated with titanium. When the polymer of the core is dissolved, the metal coating of the core may remain as a coating on the polymer matrix of the internal surfaces, for example, internal porous surfaces, of the shell after the polymer of the core is dissolved.

Figure 21C:
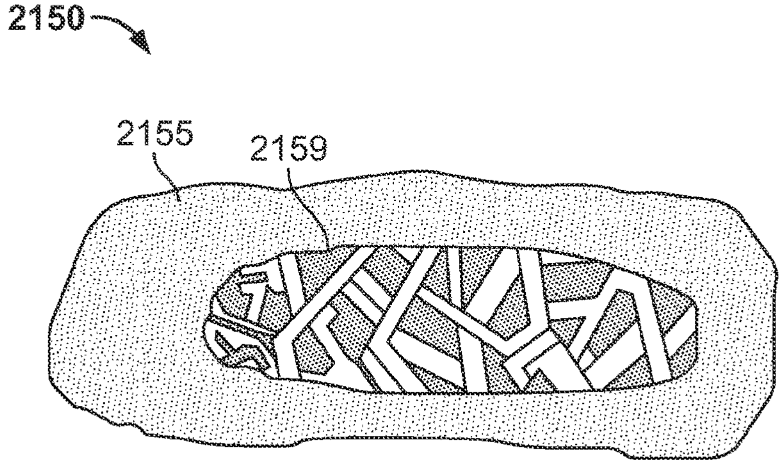
FIG. 21C is a cross-sectional view of the implant of FIG. 21A.

FIG. 21C illustrates an implant 2150 according to yet another embodiment of the disclosure. Implant 2150 may be substantially similar to implant 2100, although implant 2150 may include a shell 2155 peripherally surrounding core portion 2159, where the superior and inferior surfaces of core 2159 are exposed as part of an outer surface of implant 2150. Shell 2155 may have the same properties as shell 2105 and core portion 2159 may be made of a porous dissolvable material, similar to core portion 2109.

In another aspect, the present disclosure relates to a method of manufacture of an implant including the various implants described in the present disclosure. In some embodiments, the implants of the present disclosure may be formed using a layered additive manufacturing or a 3D printing process, e.g., using Laser Rapid Manufacturing (LRM) technology, electron beam melting (EBM), selective laser sintering (SLS), selective laser melting (SLM), and/or blown powder fusion for use with metal powders. When employing these technologies, articles are produced in layer-wise fashion from a laser-fusible powder that is dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. Detailed descriptions of the SLS technology may be found in U.S. Pat. Nos. 4,863,538, 5,017,753, 5,076,869, and 4,944,817, the entire disclosures of which are incorporated by reference herein. Similarly, a detailed description of the use of SLM technology may be found in U.S. Pat. No. 7,537,664, the disclosure of which is incorporated by reference herein.

The SLM and SLS technologies have enabled the direct manufacture of solid or porous three-dimensional articles of high resolution and dimensional accuracy from a variety of materials including wax, metal and metal alloys, metal powders with binders, polycarbonate, nylon, other plastics and composite materials, such as polymer-coated metals and ceramics. Techniques such as but not limited to SLS, three-dimensional inkjet printing (3DP), stereolithography (SLA), fused filament fabrication (FFF) and fused deposition modeling (FDM®) may be used with polymer powders or strands to produce polymeric constructs. FDM® or FFF may be used with various polymers (e.g., thermoplastics, elastomers) and waxes. Cellular scaffolds may be formed using bioplotters or 3DP. The aforementioned technologies may be used to manufacture unitary constructs that include multiple material types. For instance, implants that include a solid outer shell and a porous interior may be manufactured utilizing the described additive manufacturing technologies.

In an example of constructing a tangible structure from a model build geometry using metal powder, a layer of metal powder may be deposited onto a substrate. The substrate may be a work platform, a solid base, or a core, with the base or core being provided to possibly be an integral part of the finished product. In inkjet 3D printing, a liquid binding material is selectively deposited across a thin layer of a powder and the process is repeated in which each new layer is adhered to the previous layer. In some embodiments, individual layers of metal may be scanned using a directed high energy beam, such as a continuous or pulsed laser or e-beam system to selectively melt the powder, i.e., melt the powder in predetermined locations. Each layer, or portion of a layer, is scanned to create at least part of a predetermined porous construct, and/or at least part of a predetermined solid construct, by point exposure to the energized beam. Successive layers are deposited onto previous layers and also are scanned. The scanning and depositing of successive layers continues the building process of the predetermined solid and/or porous geometries. As disclosed herein, continuing the building process refers not only to addition of a layer of a physical construct to a previous layer but also a beginning of a new physical construct as well as the completion of the current physical construct. This leads to the production of a plurality of layers that, when combined, form the components of the implant embodiments described elsewhere herein, i.e., a final and complete implant construct.

In one embodiment, a method of manufacturing an implant, for instance implants 2100, 2150 illustrated in FIGS. 21A-C, begins with manufacture of a dissolvable core portion of the implant. The core portion is a porous structure consisting of a dissolvable material that may be additively manufactured using techniques such as those described in this disclosure. The dissolvable structure may then serve as a mold so that a shell may be formed around the dissolvable core portion. The shell may be formed through a compression molding process. After the shell is formed around the core, the core portion is dissolved so that the remaining shell is hollow with an interior void left where the dissolvable material was previously disposed.

In one example, a method of manufacturing a spinal interbody implant 2100 may comprise printing a first portion 2109 of the implant 2100, the first portion 2109 being dissolvable, compressing molding a second portion 2105 of the implant 2100 around the first portion 2109 such that the second portion 2105 entirely surrounds the first portion 2109, the second portion 2105 including a matrix of a first material and a plurality of particles distributed throughout the matrix, the plurality of particles being a second material different from the first material, and dissolving the first portion 2109 subsequent to the compression molding step.

In another example, a method of manufacturing a spinal interbody implant 2150 may comprise printing a first portion 2159 of the implant 2150, the first portion 2159 being dissolvable, compressing molding a second portion 2155 of the implant 2150 around the first portion 2159 such that the second portion 2155 entirely surrounds the first portion 2159, the second portion 2155 including a matrix of a first material and a plurality of particles distributed throughout the matrix, the plurality of particles being a second material different from the first material, and dissolving the first portion 2159 subsequent to the compression molding step.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant comprising:

an outer shell;

a fill material disposed within the outer shell; and a plurality of tubes extending from a first outer surface of the implant to a second outer surface of the implant through the fill material, the plurality of tubes including a first tube that is filled with the fill material, wherein the fill material is more porous than the outer shell and the plurality of tubes.

2. The spinal interbody implant of claim 1, wherein the plurality of tubes includes a first tube with a length entirely disposed within the fill material.

3. The spinal interbody implant of claim 2, wherein the plurality of tubes includes a second tube that extends through the outer shell and the fill material.

4. The spinal interbody implant of claim 3, wherein the second tube is non-parallel to the first tube.

5. The spinal interbody implant of claim 2, wherein the first tube and the second tube intersect.

6. The spinal interbody implant of claim 1, wherein the plurality of tubes includes a first tube with an outer surface and an inner surface, the outer surface having a shape different from the inner surface.

7. The spinal interbody implant of claim 6, wherein the outer surface is cylindrical and the inner surface is a triangular prism.

8. The spinal interbody implant of claim 6, further comprising a first channel, the first channel being non-parallel to the first tube.

9. The spinal interbody implant of claim 8, wherein the first channel extends through the outer shell and the fill material.

10. The spinal interbody implant of claim 1, wherein the outer shell and the fill material are one of titanium or a titanium alloy.

11. The spinal interbody implant of claim 1, wherein the outer shell comprises a first material and the fill material comprises a second material, the first material being the same as the second material.

12. The spinal interbody implant of claim 11, wherein the first material is titanium.

13. The implant of claim 1, wherein the plurality of tubes are solid tubular structures having a porosity less than a porosity of the fill material.

14. The implant of claim 1, wherein each of the plurality of tubes has a surface defining each of the tubes and extending through the fill material, the surface of each of the plurality of tubes having a porosity less than a porosity of the fill material.

15. A spinal interbody implant comprising:

a core portion having a first porosity, the core portion including a plurality of channels extending from a first outer surface of the core portion to a second outer surface of the core portion;

a first material layer peripherally wrapped around the core portion, the first material layer having a second porosity greater than the first porosity;

a second material layer at least partially enclosing the first material layer, the second material layer having a third porosity different from the second porosity; and an inner core portion disposed within an opening through the core portion, the opening defined by an inner wall of the core portion, wherein the inner core portion has the second porosity, wherein at least a portion of each of the core portion, the first material layer, and the second material layer are adapted to abut vertebral bodies when implanted.

16. The spinal interbody implant of claim 15, wherein the first porosity is the same as the third porosity.

17. The spinal interbody implant of claim 15, wherein the first outer surface and the second outer surface face the first material layer.

18. The spinal interbody implant of claim 15, wherein the second material layer is peripherally wrapped around the first material layer.

19. An implant comprising:

an outer shell;

a fill material disposed within the outer shell; and a plurality of tubes extending from a first outer surface of the implant to a second outer surface of the implant through the fill material, wherein the fill material is more porous than the outer shell and the plurality of tubes, and wherein the plurality of tubes includes a first tube with a length entirely disposed within the fill material, wherein the plurality of tubes includes a second tube that extends through the outer shell and the fill material, and wherein the second tube is non-parallel to the first tube.

* * * * *